(12) United States Patent
Iizuka et al.

(10) Patent No.: US 7,894,676 B2
(45) Date of Patent: Feb. 22, 2011

(54) DIAGNOSIS SUPPORT APPARATUS AND CONTROL METHOD THEREFOR

(75) Inventors: Yoshio Iizuka, Yokohama (JP); Masahiro Suzuki, Kawasaki (JP); Kazuhiro Miyasa, Yokohama (JP); Akihiro Katayama, Yokohama (JP)

(73) Assignee: Canon Kabushiki Kaisha, Tokyo (JP)

( * ) Notice: Subject to any disclaimer, the term of this patent is extended or adjusted under 35 U.S.C. 154(b) by 0 days.

(21) Appl. No.: 12/748,315

(22) Filed: Mar. 26, 2010

(65) Prior Publication Data
US 2010/0189366 A1 Jul. 29, 2010

Related U.S. Application Data

(63) Continuation of application No. PCT/JP2008/067444, filed on Sep. 26, 2008.

(30) Foreign Application Priority Data

Sep. 28, 2007 (JP) .............................. 2007-256014

(51) Int. Cl.
G06K 9/62 (2006.01)
A61B 5/00 (2006.01)
G06F 17/30 (2006.01)
(52) U.S. Cl. ..................... 382/209; 600/300; 707/769
(58) Field of Classification Search ............ 382/128, 382/129, 130, 131, 132, 133, 134, 190, 294; 378/4, 21–27, 167, 901; 600/300, 410, 411, 600/427; 128/920, 922; 707/769
See application file for complete search history.

(56) References Cited

U.S. PATENT DOCUMENTS 6,726,680 B1 * 4/2004 Knopp et al. .................. 606/12
7,187,790 B2 * 3/2007 Sabol et al. .................. 382/128

FOREIGN PATENT DOCUMENTS

| JP | H09-223129 A | 8/1997 |
| JP | 2003-033327 A | 2/2003 |
| JP | 2005-065728 A | 3/2005 |
| JP | 2006-059063 A | 3/2006 |
| JP | 2006-155002 A | 6/2006 |
| JP | 2006-181137 A | 7/2006 |
| JP | 2007-140861 A | 6/2007 |

OTHER PUBLICATIONS

"Curvature Based Internal Structure Analysis of Pulmonary Nodules Using Thoracic 3-D CT Images"; The transactions of the IEICE.

* cited by examiner

Primary Examiner—Abolfazl Tabatabai
(74) Attorney, Agent, or Firm—Canon U.S.A, Inc. I.P Division

(57) ABSTRACT

A diagnosis support apparatus includes a storage unit which stores pieces of image feature information and finding sentences as interpretation results in correspondence with each other. This apparatus acquires image feature information of a target area designated on an image to be interpreted, searches the storage unit for image feature information similar to the acquired image feature information, acquires a finding sentence stored in correspondence with the retrieved image feature information from the storage unit, and creates a finding sentence concerning interpretation of the designated target area by changing a description of the acquired finding sentence based on image feature information of the designated target area.

17 Claims, 12 Drawing Sheets

TARGET AREA

TARGET AREA

DIAGNOSIS SUPPORT APPARATUS AND CONTROL METHOD THEREFOR

CROSS REFERENCE TO RELATED APPLCIATIONS

This application is a CONTINUATION of PCT application No. PCT/JP2008/067444 filed on Sep. 26, 2008 which claims priority from the benefit of Japanese Patent Application No. 2007-256014 filed on Sep. 28, 2007, the disclosures of which are hereby incorporated by reference herein in their entirety.

TECHNICAL FIELD

The present invention relates to a diagnosis support apparatus that supports the creation of findings in interpretation or image diagnosis.

BACKGROUND ART

Recently, medical imaging apparatus such as CT (Computed Tomography) apparatus and MRI (Magnetic Resonance Imaging) apparatus have been widely used. With this widespread use, there have been an increasing need for interpretation or image diagnosis which determines the presence/absence of diseases under the expert observation of medical images.

Many medical institutions in which role assignment is practiced, such as general hospitals, have imaging technicians who perform imaging or interpretation doctors who perform interpretation or image diagnosis as well as doctors in charge of the medical treatment of patients. The workflows in such medical institutions generally include:

1. A doctor in charge gives an instruction to perform medical imaging.
2. An imaging technician performs imaging.
3. An interpretation doctor interprets captured images and summarizes interpretation results into an interpretation report.
4. The interpretation report is sent to the doctor in charge.

With advances in medical imaging apparatus, the number of medical images captured tends to increase year by year. The increasing rate of the number of interpretation doctors is, however, low as compared with the increasing rate of the number of medical images captured. For this reason, it is said that the amount of work per interpretation doctor tends to increase year by year, resulting in increased fatigue experienced by interpretation doctors. In general, people tend to make mistakes as fatigue increases. That is, the increasing fatigue by interpretation doctors may lead to an increase in oversights and misdiagnosis of diseases. Demands have therefore arisen for diagnosis support apparatus that reduces the work load on interpretation doctors.

The main work of an interpretation doctor can be roughly divided into two parts, for example, interpretation itself and interpretation report creation. Studies have been made on computer-aided diagnosis apparatus (to be referred to as CAD apparatus hereinafter) as apparatus for supporting interpretation itself. Some of them have been commercialized, such as interpretation support apparatus for mammography. However, a CAD apparatus is an apparatus for reducing the oversight of diseases and is designed based on the assumption that an interpretation doctor interprets by himself/herself first, and then the CAD apparatus displays the detected disease candidate images. This apparatus therefore cannot reduce amount of work for the interpretation doctor. Instead, this may require additional work in the form of reexamining the disease candidate images detected by the CAD apparatus.

On the other hand, studies have been made on a report creation support apparatus as an apparatus that supports interpretation report creation. The report creation support apparatus is an apparatus that inputs finding sentences more efficiently, which are normally input manually by an interpretation doctor, and is aimed at reducing the work load on the interpretation doctor who is associated with interpretation report creation.

Description items for an interpretation report are roughly divided into three classifications, namely "information obtained before interpretation", "interpretation finding", and "attachment of a copy of a slice image".

Information obtained before interpretation, which belongs to the first classification, includes at least part of
  information associated with examination (an examination ID, an examination date, an imaging apparatus, an imaging region, imaging conditions, and the like),
  information associated with a patient (a name, age, sex, and the like), and
  information associated with an examination institution and doctor (a hospital name, a medical office name, the name of a doctor in charge, an interpretation doctor, and the like). Many of these pieces of information are input or determined in advance in medical information systems such as a hospital information system (HIS) and radiology information system (RIS). Therefore, allowing these information systems to send information to a diagnosis support apparatus allows it to automatically enter these pieces of information on an interpretation report.

In an interpretation finding, which belongs to the second classification, the interpretation doctor writes his/her medical judgment about an abnormal shade, if any, on an image to be interpreted. The doctor may also write information indicating that there is no abnormality.

Attachment of a copy of a slice image, which belongs to the third classification, is to attach a copy of a slice image depicting, for example, an abnormal shade most legibly. In this case, the interpretation doctor sometimes superimposes and draws, on the copy of the slice image, a graphic pattern (an arrow indicating the abnormal shade, in general) indicating at which position or in which area on the copy of the slice image the abnormality is seen.

A general report creation support apparatus is automated to enter information obtained before interpretation, which belongs to the first classification of the above three classifications of report description items. This apparatus also allows an interpretation doctor to perform attachment of a slice image, which belongs to the third classification, with simple operation. Patent references 1, 2, and 3 have also proposed techniques associated with input support of findings, which belongs to the second classification.

Patent reference 1: Japanese Patent Laid-Open No. 2003-33327
Patent reference 2: Japanese Patent Laid-Open No. 2006-155002
Patent reference 3: Japanese Patent Laid-Open No. 2006-181137

DISCLOSURE OF INVENTION

Problems That The Invention is to Solve

However, concerning the description of "interpretation finding", the proposals made by patent references 1, 2, and 3 are still not satisfactorily efficient input support. The proposals respectively have the following problems.

Patent reference 1 discloses an apparatus that creates a tentative report model by using an image and the lesion feature amount data of the image and displaying the model on a screen. An interpretation doctor creates a tentative report based on this tentative report model. A tentative report model that can be created by this prior art is only lesion feature amount data detected by a lesion candidate detection function and displayed in text form. The invention disclosed in patent reference 1 can therefore display a simple list of information such as the detected position of a lesion candidate and a density value at the position, but is difficult to create a document including diverse expressions like those written by humans. In addition, since the lesion candidate detection function cannot always estimate accurate lesion names, the information included in a tentative report model may include errors. That is, since a tentative report model is a list of monotonic words that may include errors, if the interpretation doctor uses it as a finding sentence model, it may become necessary later to greatly revise and correct the sentence. That is, this input support function is not very effective.

According to patent reference 2, storing interpretation reports as structured reports with tags in a database makes it possible to easily search for interpretation reports created in the past with keywords. An interpretation doctor inputs keywords or a computer automatically creates keywords based on the feature amount data of automatically detected lesion candidates. The invention disclosed in patent reference 2 can search for a plurality of past interpretation reports including designated keywords, but cannot search for proper past interpretation reports unless proper keywords are designated. Furthermore, data obtained as a search result is a list of interpretation reports but are not finding sentences themselves. Therefore, the interpretation doctor needs to perform the following series of operations after keyword search:

selecting interpretation reports one by one from the list of interpretation reports displayed as the search result,
displaying and rereading the contents of each report, and
copying some sentences from the finding column of each interpretation report as needed and pasting the copied sentences on the currently edited interpretation report.

The invention disclosed in patent reference 2 may provide some help to the interpretation doctor in quoting finding sentences from past interpretation reports. However, it requires many procedures until a particular past finding sentence can be quoted, as described above. In particular, it requires a long period of time to reread past interpretation reports one by one. Therefore, this technique does not lead to an improvement in the work efficiency of an interpretation doctor, for example, a reduction in work time. That is, this prior art cannot be said to be a truly useful input support function.

Like the technique disclosed in patent reference 2, the technique disclosed in patent reference 3 is configured to store interpretation reports as structured reports with tags in a database to easily search for interpretation reports created in the past with keywords. The technique disclosed in patent reference 3 also allows a search for synonyms of keywords designated through use of a thesaurus (a dictionary of synonyms). The description of the embodiments in patent reference 3 describes that character string information stored in the header of an image file is also regarded as a target for keyword search as well as medical information written on an interpretation report, such as a patient name, examination name, and a case name. The search means in this invention is slightly extended as compared with the invention disclosed in patent reference 2. However, like the invention disclosed in patent reference 2, the invention disclosed in parent reference 3 still has the following problems:

Since this technique is basically keyword search, search results greatly vary depending on designated keywords.
Since data obtained as a search result is a list of interpretation reports, it takes a long work time to check the finding sentences of interpretation reports one by one.

The present invention has been made in consideration of the above problems, and has as its object to provide a diagnosis support apparatus and method that effectively support the creation of finding sentences that correspond to the contents of the images to be interpreted.

Means of Solving the Problems

In order to achieve the above object, a diagnosis support apparatus according to one aspect of the present invention comprises the following arrangement. That is, a diagnosis support apparatus comprises:

storage means for storing image feature information and a finding sentence as an interpretation result in correspondence with each other;

acquisition means for acquiring image feature information of a target area designated on an image to be interpreted;

search means for searching the storage means for image feature information similar to the image feature information acquired by the acquisition means and acquiring a finding sentence stored in correspondence with the retrieved image feature information from the storage means; and creation means for creating a finding sentence concerning interpretation of the designated target area by changing, based on image feature information of the target area acquired by the acquisition means, a description of the finding sentence acquired by the search means.

In order to achieve the above object, a diagnosis support apparatus according to another aspect of the present invention comprises the following arrangement. That is, a diagnosis support apparatus comprises:

storage means for storing image feature information and a finding sentence in correspondence with each other;

acquisition means for acquiring image feature information of an image to be interpreted; and search means for searching for a finding sentence stored in the storage means, based on the image feature information acquired by the acquisition means.

In order to achieve the above object, a diagnosis support method according to another aspect of the present invention is a control method for a diagnosis support apparatus comprising storage means for storing image feature information and a finding sentence as an interpretation result in correspondence with each other, comprising:

an acquisition step of acquiring image feature information of a target area designated on an image to be interpreted;

a search step of searching the storage means for image feature information similar to the image feature information acquired in the acquisition step and acquiring a finding sentence stored in correspondence with the retrieved image feature information from the storage means; and a creation step of creating a finding sentence concerning interpretation of the designated target area by changing, based on image feature information of the target area acquired in the acquisition step, a description of the finding sentence acquired in the search step.

In order to achieve the above object, a diagnosis support method according to another aspect of the present invention is a control method for a diagnosis support apparatus comprising storage means for storing image feature information and a finding sentence in correspondence with each other, comprising:

an acquisition step of acquiring image feature information of an image to be interpreted; and a search step of searching for a finding sentence stored in the storage means, based on the image feature information acquired in the acquisition step.

Effect of the Invention

According to the present invention, it is possible to effectively support the creation of finding sentences corresponding to the contents of an image to be interpreted.

Note that "target area" written in the claims of the present invention is used as a term indicating either a target area or an abnormal area in the embodiments, and is not limited to any special shape or size.

Other features and advantages of the present invention will be apparent from the following description taken in conjunction with the accompanying drawings, in which like reference characters designate the same or similar parts throughout the figures thereof.

BRIEF DESCRIPTION OF DRAWINGS

The accompanying drawings, which are incorporated in and constitute a part of the specification, illustrate embodiments of the invention and, together with the description, serve to explain the principles of the invention.

BEST MODE FOR CARRYING OUT THE INVENTION

The embodiments of the present invention will be described in detail below with reference to the accompanying drawings.

First Embodiment

Figure 1:
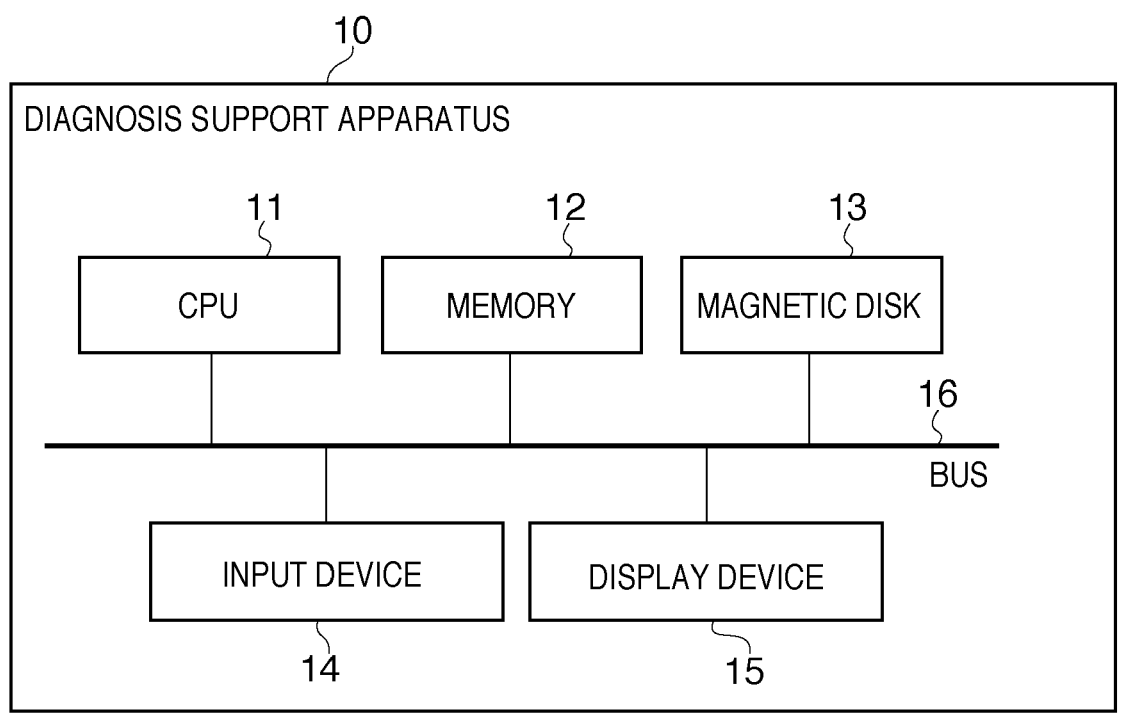
FIG. 1 is a block diagram showing the hardware arrangement of a diagnosis support apparatus according to an embodiment of the present invention.

FIG. 1 is a block diagram showing the hardware arrangement of a diagnosis support apparatus according to the first embodiment. Referring to FIG. 1, a diagnosis support apparatus 10 includes a central processing unit (CPU) 11, memory 12, magnetic disk 13, input device 14, display device 15, and bus 16.

The CPU 11 mainly controls the operation of each constituent element of the apparatus. The memory 12 stores control programs for the apparatus and provide a work area for the execution of programs. The magnetic disk 13 stores an operating system (OS), device drives for peripheral devices, various kinds of application software including programs for performing diagnosis support processing (to be described later), and the like. The input device 14 includes a keyboard for inputting character string information such as characters, numbers, symbols, and commands and a mouse which inputs pointing information such as a pointing position and a click command. Note that a plurality of each type of devices may be connected to this apparatus. The display device 15 is a monitor or display for displaying various kinds of display information such as characters, graphic patterns, and images on the screen. Note that it is possible to use, as the display devices 15, an arbitrary number of displays such as CRT displays, liquid crystal displays, and plasma displays in arbitrary combinations. The bus 16 is a communication path for the transmission/reception of data between the respective constituent elements of the apparatus, and also functions as a power line for transmitting and receiving power for operating the respective constituent elements of the apparatus.

Figure 2:
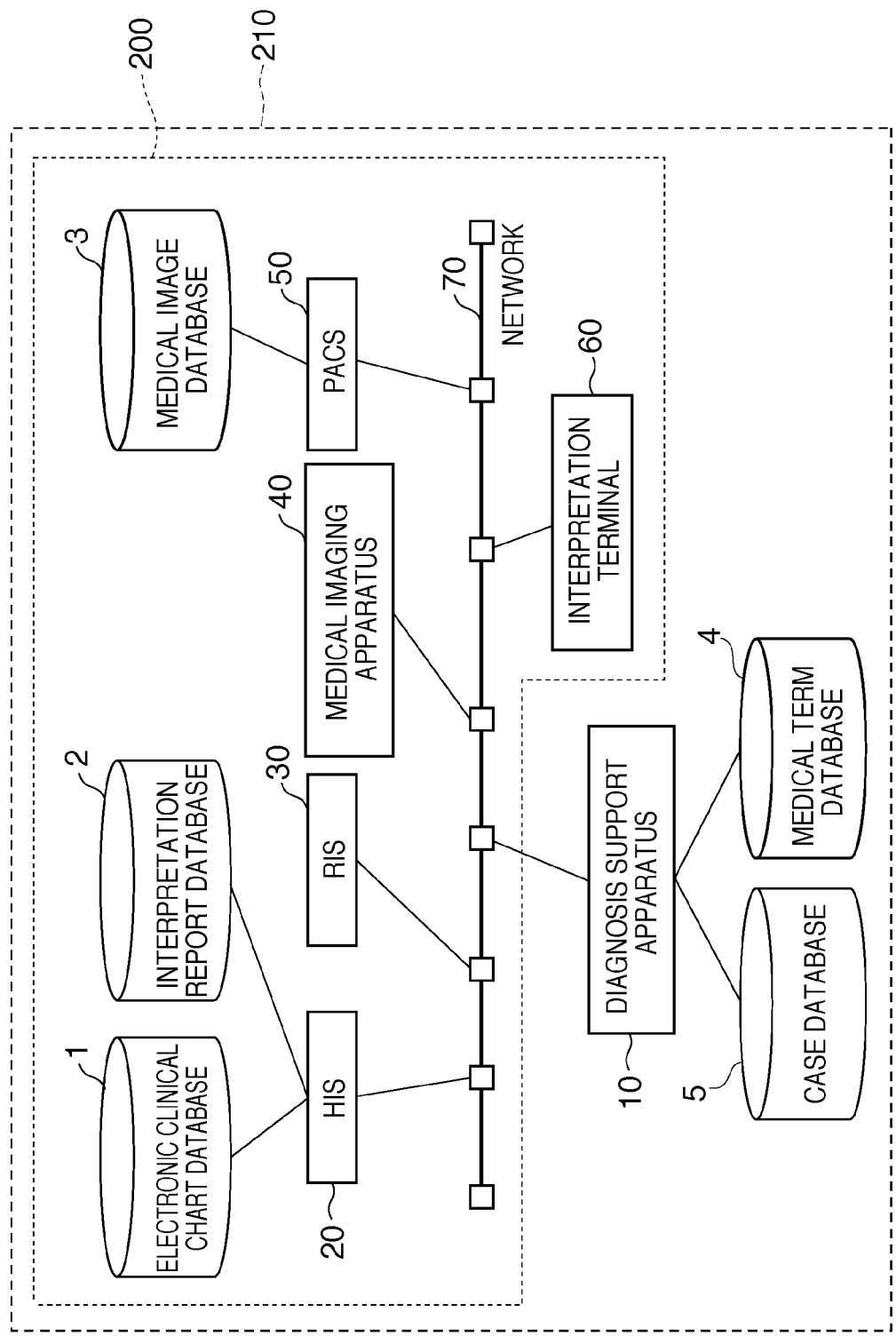
FIG. 2 is a block diagram of a system configuration showing the difference between the system configuration of a medical information system 200 including a conventional apparatus/system and the like and the system configuration of a medical information system 210 including a diagnosis support apparatus 10 according to the present invention.

FIG. 2 is a block diagram of a system configuration showing the difference between the system configuration of a medical information system 200 including a conventional apparatus and system and the system configuration of a medical information system 210 including the diagnosis support apparatus 10 according to this embodiment.

Referring to FIG. 2, the conventional medical information system 200 includes a HIS (Hospital Information System) 20,
a RIS (Radiology Information System) 30,
a medical imaging apparatus 40,
a PACS (Picture Archiving and Communication System) 50,
an interpretation terminal 60, and
a network 70.

The HIS 20 is a comprehensive system including a medical administrative assisting system, a medical treatment reservation system, and a medical treatment information system, and includes an electronic clinical chart database 1 and interpretation report database 2. The electronic clinical chart database 1 stores electronic clinical charts recording patient medical treatment information. The interpretation report database 2 stores interpretation reports created by interpretation doctors. The RIS 30 is a system for imaging reservation, interpretation management, material inventory management, and the like in a radiology department. The RIS 30 sometimes manages the interpretation report database 2.

The medical imaging apparatus 40 is a generic name for, for example,
- a simple X-ray imaging apparatus (or an X-ray apparatus),
- a CT (Computed Tomography) apparatus,
- an MRI (Magnetic Resonance Imaging) apparatus,
- a PET (Positron Emission Tomography) apparatus,
- a PET/CT apparatus,
- a SPECT (Single Photon Emission Computed Tomography) apparatus,
- an ultrasound image diagnosis apparatus,
- a fundus camera (or a fundus photography apparatus), and
- an OCT (Optical Coherence Tomography) apparatus. An arbitrary number of apparatus described above are installed for each medical institution.

The PACS 50 is a system for electronically storing, searching for, and communicating medical images captured by the medical imaging apparatus 40, and includes a medical image database 3. The interpretation terminal 60 includes various functions required for an interpretation doctor to perform interpretation. That is, the interpretation terminal 60 includes
- a medical image display function for reading out an image to be interpreted from the PACS 50 (its medical image database 3) in accordance with an instruction from the interpretation doctor and displaying the image on the monitor,
- an interpretation report creation function of displaying an interpretation report creation window and creating an interpretation report in accordance with inputs from the interpretation doctor, and
- an interpretation report display function for displaying past interpretation reports. In addition, the interpretation terminal 60 or another terminal equivalent to the interpretation terminal 60 sometimes has an electronic clinical chart display function for displaying the electronic clinical chart of a patient corresponding an image to be interpreted. This function allows to refer to the electronic clinical chart of a patient as reference information for interpretation.

In addition to the conventional medical information system 200, the medical information system 210 includes the diagnosis support apparatus 10 according to the present invention. The diagnosis support apparatus 10 uses a medical term database 4 and case database 5. The medical term database 4 is referred to when a syntax analysis unit 105 analyzes a finding sentence. The case database 5 stores image feature information and finding sentences as interpretation results in correspondence with each other. Note that the hardware arrangement of the interpretation terminal 60 can be the same as that of the diagnosis support apparatus 10 shown in FIG. 1. Therefore, implementing some or all of the functions of the diagnosis support apparatus 10 into the interpretation terminal 60 can integrate the diagnosis support apparatus 10 and the interpretation terminal 60 into one apparatus. The medical term database 4 and the case database 5 are required to be accessible from the diagnosis support apparatus 10, and hence need not always be operated under the control of the diagnosis support apparatus 10.

The function of the diagnosis support apparatus 10 according to the first embodiment and a processing procedure in the apparatus will be described below with reference to FIGS. 3 to 9.

Figure 3:
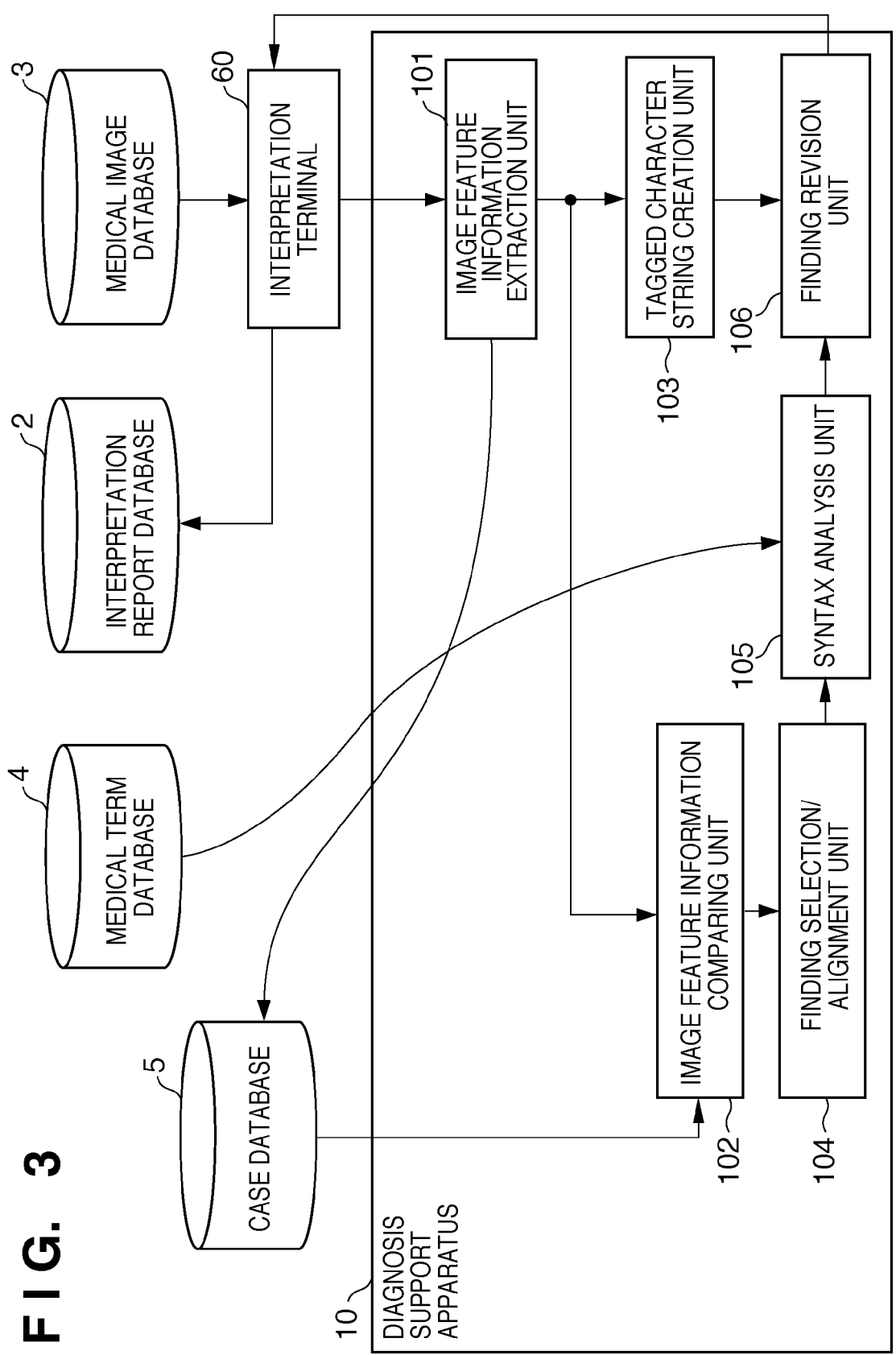
FIG. 3 is a functional block diagram for explaining the main functions of the diagnosis support apparatus 10 according to the first embodiment of the present invention.

FIG. 3 is a functional block diagram for explaining the main functions of the diagnosis support apparatus 10 according to the first embodiment. For the sake of descriptive convenience, the upper half of FIG. 3 shows some of the constituent elements of the medical information system 210 shown in FIG. 2.

Figure 4:
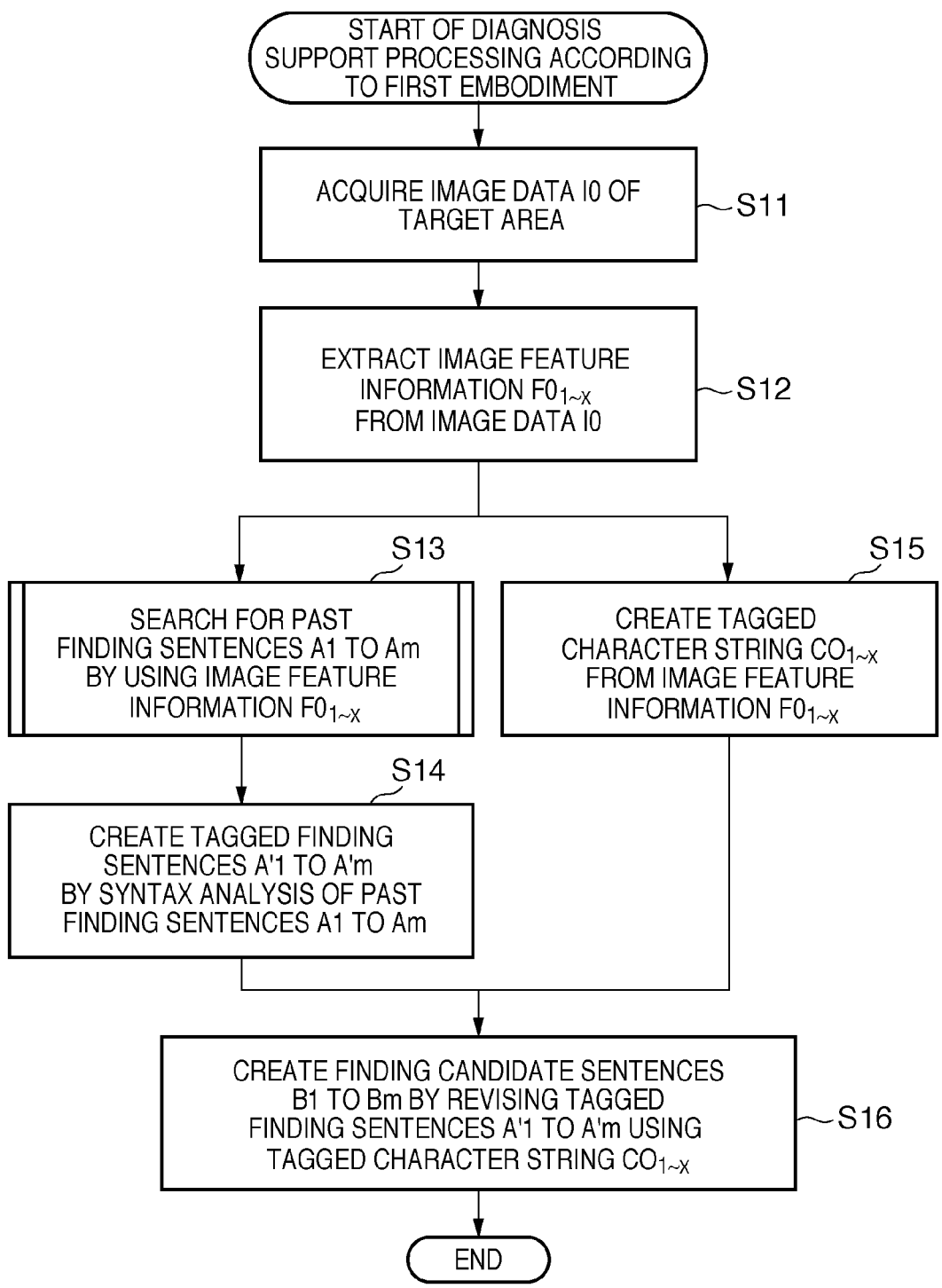
FIG. 4 is a flowchart showing a diagnosis support processing procedure in the diagnosis support apparatus 10 shown in FIG. 3.
Figure 5:
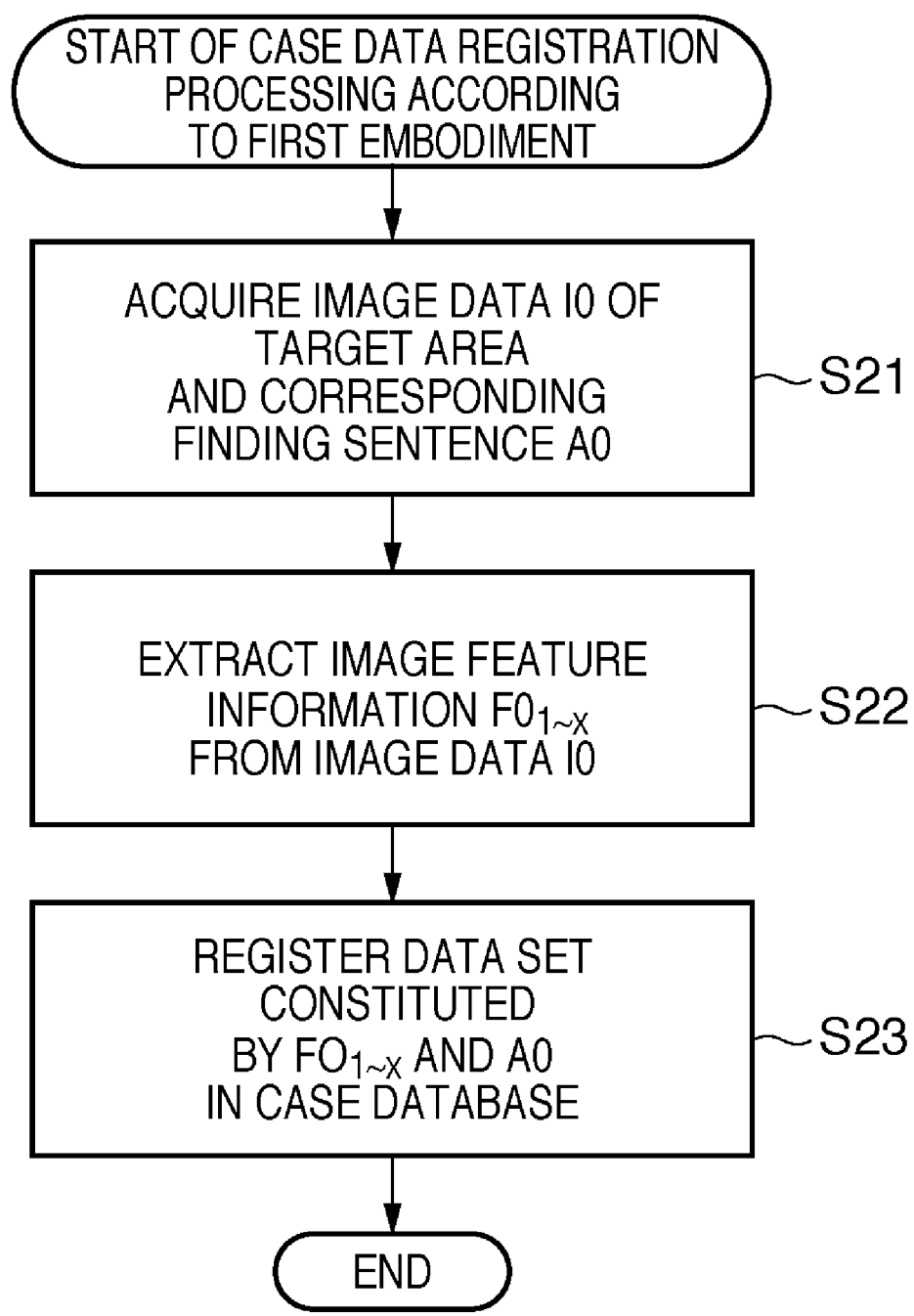
FIG. 5 is a flowchart showing a detailed procedure in step S13 in diagnosis support processing in the diagnosis support apparatus 10 shown in FIG. 3.
Figure 6:
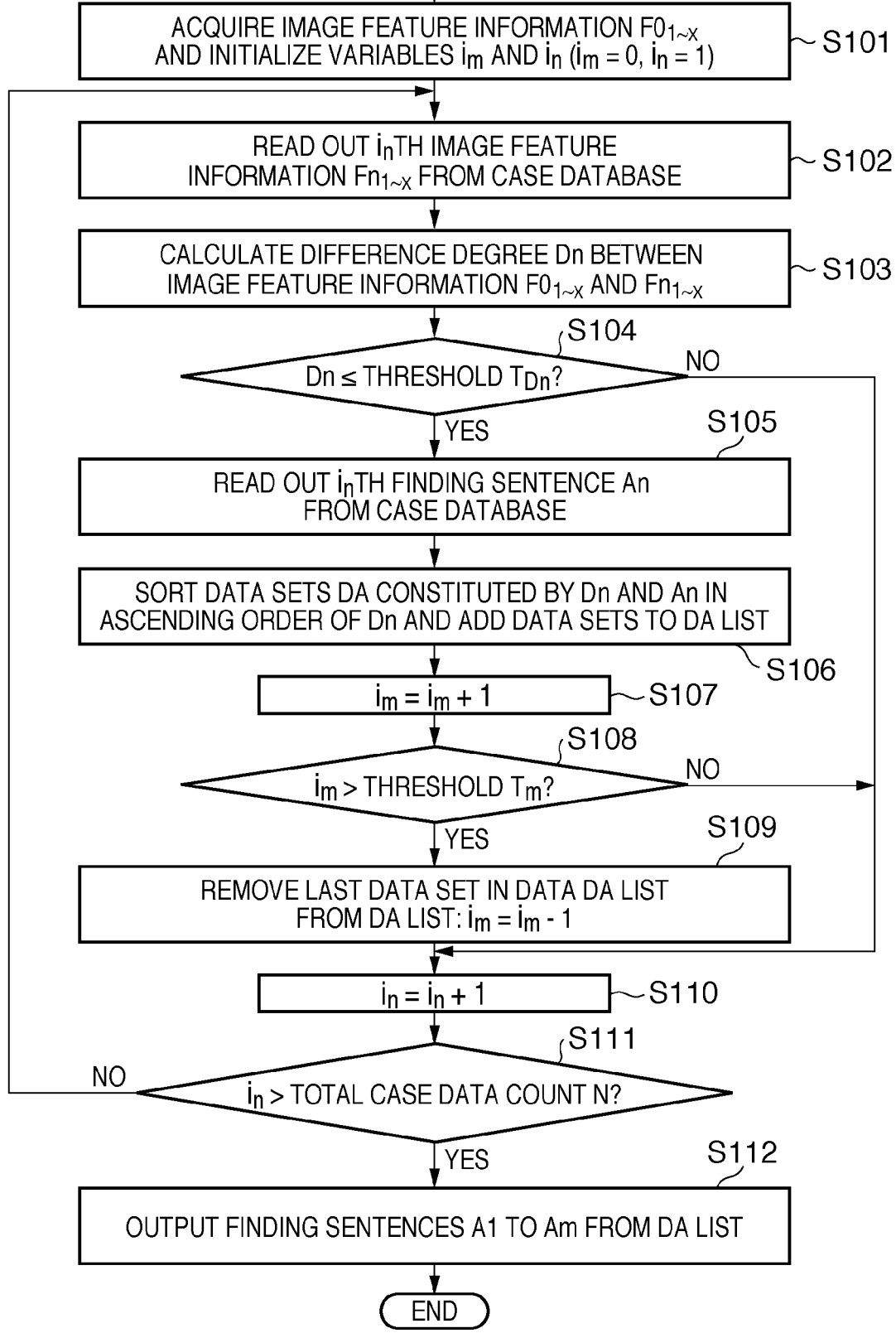
FIG. 6 is a flowchart showing a case data registration processing procedure in the diagnosis support apparatus 10 shown in FIG. 3.

FIGS. 4 to 6 are flowcharts showing a processing procedure in the diagnosis support apparatus 10 shown in FIG. 3. FIG. 4 shows a procedure in diagnosis support processing. FIG. 6 shows a detailed procedure in step S13 in the diagnosis support processing. FIG. 5 shows a procedure for case data registration processing.

Figure 7:
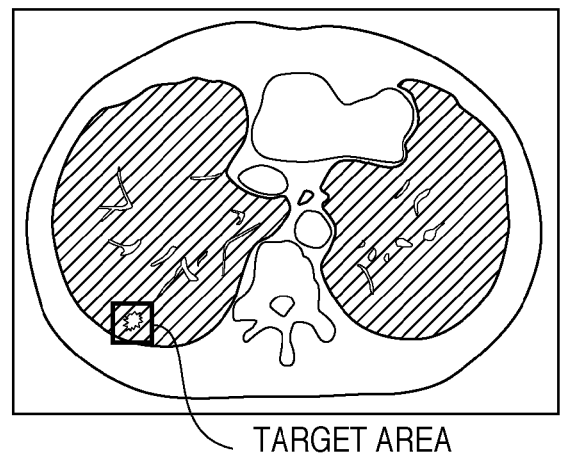
FIG. 7 is a view showing an example of the medical image captured by a medical imaging apparatus 40 and a target area on the image.
Figure 8:
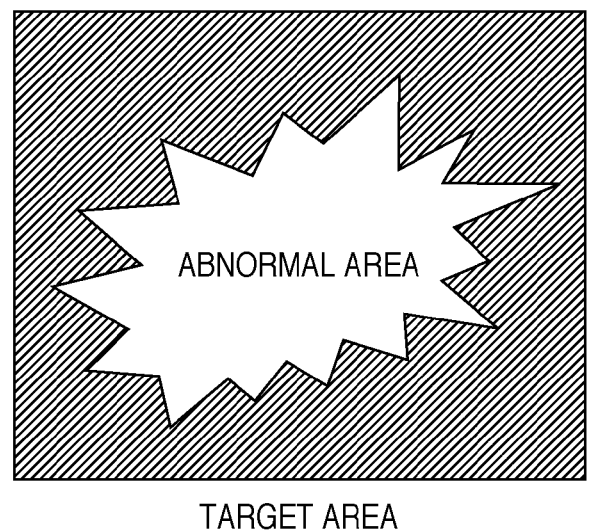
FIG. 8 is an enlarged view of the target area shown in FIG. 7.
Figure 9:
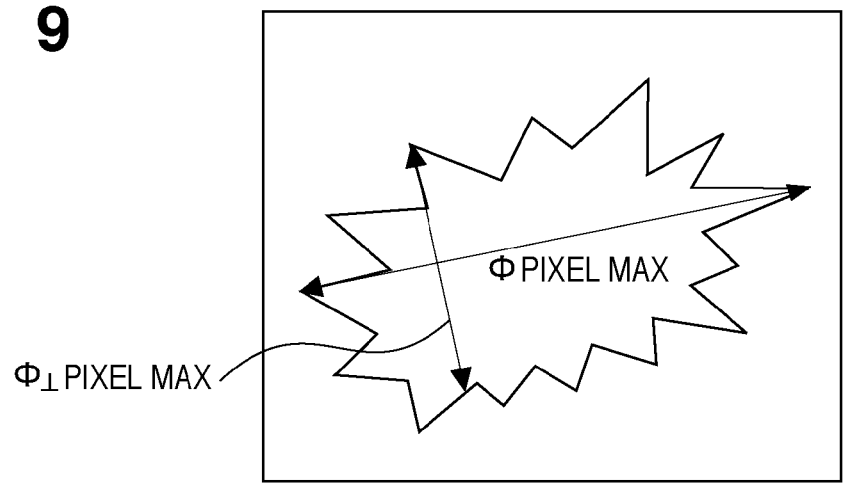
FIG. 9 is a view for explaining a method of calculating one piece of image feature information of an abnormal area shown in FIG. 8.

FIG. 7 is a view showing an example of a medical image captured by the medical imaging apparatus 40 and a target area on the image. FIG. 8 is an enlarged view of the target area shown in FIG. 7. FIG. 9 is a view for explaining a method of calculating one piece of image feature information of an abnormal area schematically shown in FIG. 8.

Referring to FIG. 3, the diagnosis support apparatus 10 operates while communicating with the interpretation terminal 60. A communication protocol is determined in advance between the diagnosis support apparatus 10 and the interpretation terminal 60. The interpretation terminal 60 transmits/receives data to/from the diagnosis support apparatus 10 in accordance with the predetermined protocol.

Note that when creating an interpretation report, first of all, the interpretation doctor reads out an image to be interpreted from the medical image database 3 by using the interpretation terminal 60, and interprets the image upon displaying it on the monitor of the interpretation terminal 60. The interpretation doctor then enters findings in an interpretation report, and stores the interpretation report in the interpretation report database 2 upon completing the interpretation report. Conventionally, the interpretation doctor enters findings in an interpretation report by directly typing character strings with the keyboard of the interpretation terminal 60. In contrast, the diagnosis support apparatus 10 according to the first embodiment automatically creates sentences as finding sentence candidates, as described later. This allows the interpretation doctor to create finding sentences with simple operation, and hence greatly improves the efficiency of interpretation report creation operation.

Referring to FIG. 3, when the interpretation doctor designates a target area on the image to be interpreted which is displayed on the monitor of the interpretation terminal 60 by using the mouse or the like as shown in FIG. 7, the interpretation terminal 60 transmits image data I0 included in the target area to the diagnosis support apparatus 10. The diagnosis support apparatus 10 starts the diagnosis support processing shown in FIG. 4 upon receiving the image data I0 of the target area.

First of all, an image feature information extraction unit 101 in FIG. 3 extracts image feature information $F0_{1 \sim x}$ from the image data I0 of the target area (step S12 in FIG. 4) after acquiring (receiving) the image data I0 (step S11 in FIG. 4).

A method of extracting the image feature information $F0_{1 \sim x}$ will be described below. The image feature information $F0_{1 \sim x}$ is complex information constituted by pieces of image feature information $F0_1, F0_2, \ldots, F0_x$ as pieces of information of x ($x \geq 1$) feature items. It is preferable to select, as such information, information which can adequately express each image feature of the image data I0 of the target area. As the pieces of image feature information $F0_1$ to $F0_x$, for example, the following pieces of information can be used:

$F0_1$=body region name or body region code to which target area belongs $F0_2$=maximum diameter of abnormal area $F0_3$=ratio between area of abnormal area and length of contour line $F0_4$=circularity or oblateness of abnormal area $F0_5$=frequency characteristic of luminance distribution of target area $F0_6$=luminance distribution pattern of abnormal area $F0_7$=contrast ratio between inside and outside of boundary of abnormal area . . . (1)

Note that the abnormal area in the above description is an indefinite area having a shade distribution from which a disease is suspected, as shown in FIG. 8. In general, as shown in FIGS. 7 and 8, the interpretation doctor designates a rectangle surrounding an abnormal area as a target area.

The interpretation terminal 60 may acquire the image feature information $F0_1$ in advance and transmit it to the diagnosis support apparatus 10, together with the image data I0 of the target area, or may acquire the information from the diagnosis support apparatus 10.

When the interpretation terminal 60 is to acquire the image feature information $F0_1$ in advance, the interpretation doctor may directly input a body region name (or code) into the interpretation terminal 60. Alternatively, it is possible to automatically recognize a body region by using the following image processing technique. The following is an example of a method of automatically recognizing a body region.

Medical images to be generally handled conform to the DICOM standard as an international standard associated with the storage and communication of medical images, and imaging conditions are stored in the header portion (DICOM header) of a DICOM image. Therefore, checking the imaging conditions written in a DICOM header makes it possible to roughly know a body region such as a chest region, abdominal region, or breast. It is also possible to segment a medical image into areas for almost each organ by segmenting the image into a plurality of areas by performing multi-threshold processing for the luminance values of the medical image or performing area segmentation using an area segmentation technique such as the level set method or the snakes method. Thereafter, collating the shape of an area and the relative position of the area with preliminary knowledge makes it possible to estimate which area corresponds to which organ. With these processes, it is possible to automatically estimate a body region to which a designated target area belongs on an organ basis.

When the diagnosis support apparatus 10 is to acquire the image feature information $F0_1$, the interpretation terminal 60 needs to transmit not only the image data I0 of the target area but also medical image data to be interpreted to the diagnosis support apparatus 10. In this case, the interpretation terminal 60 may transmit information indicating the storage location of the medical image data instead of the medical image data itself. The diagnosis support apparatus 10 can acquire or estimate information of a body region to which the target region belongs from the medical image data to be interpreted by using the same method as that described above as the processing to be performed by the interpretation terminal 60.

When the pieces of image feature information $F0_2$ to $F0_7$ are to be obtained, an abnormal area must be extracted in advance by segmenting the target area in advance. To segment a target area, the method described in the description of the image feature information $F0_1$ can be used. That is, it is possible to segment a target area into a plurality of areas by performing multi-threshold processing for the luminance values of the image or to segment the target area by using an area segmentation technique such as the level set method or the snakes method.

The image feature information $F0_2$ is information indicating the size of the abnormal area. If, for example, the abnormal area is a progressive disease such as a cancer, this is very important information indicating the degree of progress of the disease. The following is an example of a method of calculating the image feature information $F0_2$. Two different pixels are selected on the boundary line of an extracted abnormal area, and the straight distance between the two pixels is calculated on a pixel count basis. This processing is performed for all combinations of two pixels. The maximum value among the calculated values is selected. Letting $\phi_x$ and $\phi_y$ be the distances between two pixels in the x and y directions on a pixel count basis, a distance $\phi_{pixel}$ between the two pixels on a pixel count basis can be given by $$\phi_{pixel}=(\phi_x^2+\phi_y^2)^{1/2} \quad (2)$$

Although the maximum diameter $\phi_{pixel\,max}$ value on a pixel count basis obtained in this manner can be substituted as the image feature information $F0_2$ value, further checking imaging conditions for the medical image and lengths (width and height) Lx and Ly of one pixel in the x and y directions can calculate the actual maximum diameter by using $$F0_2=((Lx*\phi_x)^2+(Ly*\phi_y)^2)^{1/2} \quad (3)$$

The image feature information $F0_3$ is information indicating the complexity of the shape of the abnormal area. If, for example, the abnormal portion is one of diseases having various shapes such as a cancer, this information is very important information serving as an index indicating the malignancy or character of the disease.

The image feature information $F0_3$ is calculated as the ratio between a pixel count $N_{abnormal\,area}$ included in the abnormal area and a pixel count $N_{contour\,line}$ positioned on the boundary line (contour line) of the abnormal area by $$F0_3=N_{contour\,line}/N_{abnormal\,area} \quad (4)$$

Alternatively, it is possible to use the reciprocal of the above equation.

The image feature information $F0_4$ is information indicating the peround of the abnormal area. Like the image feature information $F0_3$, this information is an index for the determination of the malignancy or character of the disease. There are several methods of calculating the image feature information $F0_4$. The method exemplified in FIG. 9 uses a maximum diameter $\phi_{pixel\,max}$ of the above abnormal area. In this method, the distance between two pixels in a direction perpendicular to the direction in which maximum diameter $\phi_{pixel\,max}$ is provided. A maximum value $\phi\perp_{pixel\,max}$ of the calculated distances is obtained. The image feature information $F0_4$ is then obtained as the ratio between $\phi_{pixel\,max}$ and $\phi\perp_{pixel\,max}$ as follows:

$$F0_4=\phi\perp_{pixel\,max}/\phi_{pixel\,max} \quad (5)$$

The image feature information $F0_5$ is information indicating the luminance distribution characteristic of the target area. Like the image feature information $F0_3$, this information is an index for the determination of the malignancy or character of the disease. The image feature information $F0_5$ differs from the image feature information $F0_3$ and the image feature information $F0_4$ in that it gives no consideration to the boundary line of the abnormal area, and hence is advantageous of being free from the influence of the quality of the area segmentation method used for the abnormal area. The frequency characteristic of the luminance distribution is obtained by performing two-dimensional frequency transform of the pixel values in the target area. Frequency transform methods include fast Fourier transform (FFT), discrete cosine transform (DCT), and wavelet transform. It is possible to use any of these methods. Note however that the pieces of image feature information $F0_1$ to $F0_4$ described above are obtained as real numbers, but the frequency characteristic is obtained as a two-dimensional coefficient string (matrix). For this reason, it is difficult to compare the frequency characteristic with other information. For this reason, the frequency characteristic is further analyzed to be transformed into a real number based on a predetermined rule. For example, it is possible to define the image feature information $F0_5$ as the sum of all the two-dimensional frequency components weighted in accordance with their orders. In this case, if, for example, larger weights are used in proportion to the orders, the value of the image feature information $F0_5$ increases with an increase in the number of high-frequency components.

The image feature information $F0_6$ is information indicating the luminance distribution characteristic of the abnormal area. Like the image feature information $F0_3$, this information is an index for the determination of the malignancy or character of the disease. If the magnitudes of the respective pixel values in the abnormal area are compared to the undulations of a land, the image feature information $F0_6$ can be regarded as information indicating the undulating shape of the land. There are several methods of calculating the image feature information $F0_6$. For example, it is possible to use "shape index" values and "curvedness" values written in research paper 1 described below. Note that research paper 1 includes the description that "shape index" values and "curvedness" values are quoted from research paper 2 and research paper 3.

[Research Paper 1]: Kawada, Niki, and Omatsu, "Curvature Based Internal Structure Analysis of Pulmonary Nodules Using Thoracic 3-D CT Images", The transactions of the IEICE, D-II, Vol. J83-D-II, No. 1, pp. 209-218, January 2000

[Research Paper 2]: J. J. Koenderink and A. J. V. Doorn, "Surface Shape and curvature scales", Image and Vision Computing, vol. 10, no. 8, pp. 557-565, 1992

[Research Paper 3]: C. Dorai and A. K. Jain, "COSMOS—A Representation scheme for 3-D free-form objects", IEEE Trans. Pattern Analysis and Machine Intelligence, Vol. PAMI-19, no. 10, pp. 1115-1130, 1997

The image feature information $F0_7$ is information indicating the clarity of the boundary of the abnormal area. Like the image feature information $F0_3$, this information is an index for the determination of the malignancy or character of the disease. The image feature information $F0_7$ can be calculated as the contrast ratio between pixels adjacent to the inside and outside of the boundary line of the abnormal area in the following manner.

Letting $H_{in.ave}$ be the average luminance value of all the pixels adjacent to the inside of the boundary line of the abnormal area, and $H_{out.ave}$ be the average luminance value of all the pixels adjacent to the outside of the boundary line of the abnormal area, the image feature information $F0_7$ can be obtained as the ratio between $H_{in.ave}$ and $H_{out.ave}$.

$$F0_7 = H_{in.ave}/H_{out.ave} \quad (6)$$

It is possible to extract the pieces of image feature information $F0_1$ to $F0_7$ in the above manner. In this manner, the image feature information extraction unit 101 acquires the pieces of image feature information of the target area (abnormal area) designated on the image to be interpreted.

Now refer back to FIGS. 3 to 6. The processing in the image feature information extraction unit 101 in FIG. 3 has already been described up to the execution of steps S11 and S12 in FIG. 4.

An image feature information comparing unit 102 and a finding selection/alignment unit 104 in FIG. 3 operate in cooperation with each other to execute step S13 in FIG. 4. In step S13, the image feature information comparing unit 102 searches the case database 5 by using the image feature information $F0_{1-x}$ obtained in step S12, and reads out past finding sentences A1 to Am accumulated in the case database 5. That is, the image feature information comparing unit 102 retrieves image feature information similar to the image feature information acquired by the image feature information extraction unit 101 from the case database 5, and acquires, from the case database 5, past finding sentences stored in correspondence with the retrieved image feature information. When searching for similar image feature information, the image feature information comparing unit 102 calculates the similarity between image feature information of the target area and image feature information stored in the case database 5. A detailed processing procedure in step S13 will be described with reference to the flowchart of FIG. 6. The image feature information comparing unit 102 executes the processing from step S101 to step S105 in FIG. 6. The finding selection/alignment unit 104 executes the processing from step S106 to step S112.

In step S101 in FIG. 6, the image feature information comparing unit 102 receives the image feature information $F0_{1-x}$ from the image feature information extraction unit 101, and initializes variables $i_m$ and $i_n$ with the values 0 and 1, respectively.

$$i_m=0, i_n=1 \quad (7)$$

In step S102, the image feature information comparing unit 102 reads out image feature information $Fn_{1-x}$ included in the $i_n$th case data from the case database 5. Note that the $i_n$th case data stored in the case database 5 is a data set FA constituted by the image feature information $Fn_{1-x}$ and a finding sentence An. Note that the image feature information $Fn_{1-x}$ is complex information having pieces of image feature information $Fn_1$ to $Fn_x$.

In step S103, the image feature information comparing unit 102 calculates a difference degree Dn between the image feature information $F0_{1-x}$ and the image feature information $Fn_{1-x}$. In this case, the difference degree Dn indicates the degree of non-similarity. The difference degree Dn is a value having a meaning opposite to that of similarity, but is synonymous with similarity in a broad sense. In this specification, such a difference degree is a kind of similarity. Although it is possible to calculate a similarity indicating the degree of similarity, using the difference degree Dn will slightly simplify the processing to be described later. This embodiment therefore uses the difference degree Dn. Note that the image feature information $F0_{1-x}$ is information extracted from the target area on the medical image under interpreted. The image feature information $Fn_{1-x}$ is the nth image feature information accumulated in the case database 5, for example, information extracted from the target area on the medical image interpreted in the past. That is, the difference degree Dn is information indicating the degree to which the target area on the image under interpretation differs from the target area on the past image. For example, this information is calculated by the following method.

As described above, the image feature information $F0_{1-x}$ is complex information constituted by the pieces of image feature information $F0_1, F0_2, \ldots, F0_x$. Likewise, the image feature information $Fn_{1-x}$ is complex information constituted by the pieces of image feature information $Fn_1, Fn_2, \ldots, Fn_x$. The difference degree Dn between $F0_{1-x}$ and $Fn_{1-x}$ can be defined as the linear sum of the differences between the respective pieces of image feature information. Although the difference degree Dn can be defined by using another linear function or nonlinear function, the following description uses the linear sum for the sake of simplicity.

$$Dn = w_1|F0_1 - Fn_1| + w_2|F0_2 - Fn_2| + \ldots + w_x|F0_x - Fn_x| \quad (8)$$

where | | is a symbol indicating an absolute value, and $w_1$ to $w_x$ are weighting constants (real numbers) by which the differences between the respective pieces of image feature information are multiplied, and which are set in advance to satisfy the condition of $w_1+w_2+ \ldots +w_x=1$.

Note that $F0_1$ exemplified by equation (1) is a body region name or body region code, and hence the first term of the right-hand side of equation (8) cannot be calculated as it is. There are two measures against this. The first measure is to simply eliminate the first term of the right-hand side. The second measure is to define in advance, as a real number, the distance between each of all body region names or body region codes and a corresponding one of the remaining body region names or body region codes and substitute the corresponding distance into $|F0_1-Fn_1|$. The respective body regions have an inclusive relationship or a physical positional relationship. For this reason, it is possible to define real numbers in accordance with the inclusive relationship or physical distances between the respective regions in the body.

In step S104, the image feature information comparing unit 102 compares the difference degree Dn with a predetermined threshold $T_{Dn}$. If the difference degree Dn is equal to or less than $T_{Dn}$ (the similarity is high), the process advances to step S105. If the difference degree Dn is larger than $T_{Dn}$ (the similarity is low), the process advances to step S110.

Upon determining in step S105 that the similarity is high, the image feature information comparing unit 102 reads out the past finding sentence An included in the $i_n$th case data from the case database 5. In step S106, the finding selection/alignment unit 104 receives the difference degree Dn and the finding sentence An together from the image feature information comparing unit 102, and creates a data set DA constituted by Dn and An. The finding selection/alignment unit 104 holds a list for the storage of a plurality of data sets DA (to be simply referred to as a DA list hereinafter), and adds the previously created data sets DA to the DA list while sorting (rearranging) them in ascending order to the difference degree Dn (in descending order of similarity).

In step S107, the value of the variable $i_m$ is incremented by one.

$$i_m=i_m+1 \quad (9)$$

In step S108, the finding selection/alignment unit 104 compares the variable $i_m$ with a predetermined threshold $T_m$. If $i_m$ is larger than $T_m$, the process advances to step S109. In contrast to this, if $i_m$ is equal to or less than $T_m$, the process advances to step S110. In this case, the threshold $T_m$ is a value that limits the maximum number (the maximum value of m) of finding sentences A1 to Am.

Immediately before the execution of step S109, the DA list holds $T_m+1$ data sets. For this reason, in step S109, the finding selection/alignment unit 104 deletes one data set held at the end of the DA list to limit the number of data sets in the list to $T_m$. The finding selection/alignment unit 104 also decrements the value of the variable $i_m$ by one. As a consequence, the variable $i_m$ becomes equal to the number of data sets in the DA list.

$$i_m=i_m-1 \quad (10)$$

In step S110, the value of the variable $i_n$ is incremented by one.

$$i_n=i_n+1 \quad (11)$$

In step S111, the finding selection/alignment unit 104 compares the variable $i_n$ with a total count N of case data stored in the case database 5. If the comparison result shows that $i_n$ is larger than N (all the case data have been processed), the process advances to step S112. In contrast, if $i_n$ is equal to or less than N (there is case data which has not been processed), the process returns to step S102 to process the remaining case data. In step S112, the finding selection/alignment unit 104 reads out the finding sentences A1 to Am from all the data sets in the DA list, and transfers them to the syntax analysis unit 105 in FIG. 3.

As described above, the image feature information comparing unit 102 and the finding selection/alignment unit 104 operate in cooperation with each other to calculate the similarity between image feature information of a target area and image feature information stored in the case database 5. A finding sentence stored in correspondence with the image feature information which corresponds to the calculated similarity exceeding the threshold is acquired from the case database 5.

The interpretation doctor changes the description of the finding sentence acquired from the case database 5 in the above manner based on the image feature information of the target area acquired by the image feature information extraction unit 101, and creates a finding sentence based on interpretation of the target area. These processes are implemented by cooperation of the syntax analysis unit 105, a tagged character string creation unit 103, and a finding revision unit 106. This processing will be described below.

The syntax analysis unit 105 in FIG. 3 receives the finding sentences A1 to Am from the finding selection/alignment unit 104 and then performs syntax analysis of each finding sentence by referring to the medical term database 4, thereby extracting a description corresponding to each feature item of the image feature information. The syntax analysis unit 105 finds terms corresponding to the pieces of image feature information $Fn_1, Fn_2, \ldots, Fn_x$ described above by syntax analysis, and assigns each extracted term with a dedicated tag determined in advance for each image feature information. In addition, the syntax analysis unit 105 analyzes other terms to determine to which parts of speech (subject, predicate, object, adjective, propositional particle, adverb, and the like) the respective terms correspond, and assigns the terms with tags representing the corresponding parts of speech. In this manner, the syntax analysis unit 105 creates tagged finding sentences A'1 to A' m. In this case, a conventional technique can be used as a syntax analysis method. For example, it is possible to use the method described in patent reference 3. Alternatively, since free syntax analysis software or commercial syntax analysis software is available, it is possible to use such software.

Alternatively, since not many pieces of image feature information are expected to appear in the finding sentences A1 to Am, tags may be assigned to only limited pieces of image feature information such as a body region name ($Fn_1$) and an abnormal area size ($Fn_2$). In this case, it is possible to search the finding sentences A1 to Am for only character strings representing body region names and abnormal area sizes (combinations of numbers and character strings indicating the units of length) in advance and assign tags to only the character strings.

In addition, if pieces of image feature information are numbers, a table of correspondence between numbers which the pieces of image feature information can take and expressions (character strings) indicated by the numbers is formed in advance. Analyzing the finding sentences A1 to Am by using this table of correspondence can search the document expressions freely described by the interpretation doctor for expressions corresponding to specific pieces of image feature information. For example, in the case of the pieces of image feature information indicated by equation (1), it is possible to make an expression such as "circular", "elliptic", or "flat" correspond to the image feature information $F0_3$ in accordance with the magnitude of the circularity ratio of the abnormal area represented by the image feature information $F0_3$. In another case, it is possible to make an expression such as "boundary is clear", "boundary is slightly unclear", or "boundary is unclear" correspond to the image feature information $F0_7$ in accordance with the magnitude of the contrast ratio inside and outside the boundary of the abnormal area represented by the image feature information $F0_7$.

The tagged character string creation unit 103 in FIG. 3 receives the image feature information $F0_{1-x}$ from the image feature information extraction unit 101 and then transforms each of the pieces of image feature information $F0_2$, $F0_2$, ..., $F0_x$ into a tagged character string $C0_{1-x}$ assigned with a dedicated tag. This processing corresponds to step S15 in FIG. 4. In order to described a method of transforming each of the pieces of image feature information $F0_2$, $F0_2$, ..., $F0_x$ into a character string, a method of transforming each of the pieces of image feature information $F0_2$, $F0_2$, ..., $F0_7$ exemplified by equation (1) into a character string will be described below.

The image feature information $F0_2$ is a body region name (character string) or a body region code (numerical value or number) to which the target region belongs. If this information is a body region name, the body region name used as it is. If the information is a body region code, the body region code is transformed into a body region name by searching a table of correspondence between body region codes and body region names, which is prepared in advance.

The image feature information $F0_2$ is data which has the unit of length and is represented by a numerical value or number. If this information is represented by a numerical value, the numerical value may be transformed into a number (character string) based on a transformation rule determined for each character code. If the information is represented by a number, the number (character string) is used as it is. In addition, a character string (m, cm, or the like) representing the unit of length may be added to the end of the character string.

Since the remaining pieces of image feature information $F0_3$ to $F0_7$ are also data represented by numerical values or numbers, they can be processed basically in the same manner as for the image feature information $F0_2$. Note however that in general, these image feature amounts are hardly written in numbers in finding sentences. As for the operation of the syntax analysis unit 105, as described above, it is preferable to create, in advance, a table of correspondence between numbers which pieces of image feature information can take and expressions (character strings) represented by the numbers and transform numbers into character strings by using the table of correspondence.

The tagged character string $C0_{1-x}$ ($C0_1$, $C0_2$, ..., $C0_x$) created in this manner is transferred to the finding revision unit 106.

The finding revision unit 106 executes the processing in step S16 in FIG. 4. That is, the finding revision unit 106 receives the tagged finding sentences A'1 to A'm created by the finding selection/alignment unit 104 (step S14) and the tagged character strings $C0_1$, $C0_2$, ..., $C0_x$ created by the tagged character string creation unit 103 (step S15). The finding revision unit 106 then creates finding candidate sentences B1 to Bm by the following method using the tagged finding sentences A'1 to A'm and the tagged character strings $C0_1$, $C0_2$, ..., $C0_x$.

The finding revision unit 106 checks all the tags in the tagged finding sentences A'1 to A'm. Upon finding tags indicating the pieces of image feature information $Fn_1$ to $Fn_x$, the finding revision unit 106 replaces the character strings in the finding sentences A'1 to A'm with the tagged character strings (some of $C0_1$ to $C0_x$) corresponding to the tags, thereby creating finding candidate sentences B1 to Bm. Note however that some of the created finding candidate sentences B1 to Bm may be completely identical to each other. The finding revision unit 106 therefore compares the character strings of the finding candidate sentences B1 to Bm, and unifies identical finding candidate sentences, if any, into one sentence (leaving one finding sentence and removing the remaining identical finding sentences). That is, the finding revision unit 106 removes candidate finding sentences having the same contents from a plurality of candidate finding sentences.

In order to exemplify changes in the finding sentences created by the above processing, the following shows the case of the finding sentences A1 to A4 in the DA list, the tagged character string $C0_{1-2}$, and the finding candidate sentences B1 to B3. Note that the character strings enclosed by "[ ]" in the finding sentences A1 to A4 are character strings to be replaced by the tagged character string $C0_1$, and the character strings enclosed by "{ }" are character strings to be replaced by the tagged character string $C0_2$.

A1: "A solid nodule having {a size of 20 mm} is found in [the left superior lobe]."

A2: "A solid nodule having {a size of about 11 mm} is found in [the right superior lobe]."

A3: "A nodule is found in [the right inferior lobe]. {a size of about 14 mm}. It is a high-density nodule with a clear boundary."

A4: "There is a nodule accompanied by a glassy shade having {a size of about 25 to 30 mm} in [the right superior lobe S1]."

$C0_1$: "left inferior lobe"

$C0_2$: "a size of 17 mm"

B1: "A solid nodule having a size of 17 mm is found in the left inferior lobe."

B2: "A nodule is found in the left inferior lobe. A size of 17 mm. It is a high-density nodule with a clear boundary."

B3: "There is a nodule accompanied by a glassy shade having a size of 17 mm in the left inferior lobe."

When the finding candidate sentences B1 to Bm created by the finding revision unit 106 are transmitted to the interpretation terminal 60, the diagnosis support apparatus 10 terminates the diagnosis support processing.

In the above manner, the syntax analysis unit 105 extracts each of the plurality of finding sentences acquired from the case database 5, and the finding revision unit 106 changes the description of each tagged feature item based on the contents of each feature item of the image feature information of the target area. In this manner, a plurality of finding candidate sentences are created and displayed on the display device 15.

Alternatively, a plurality of finding candidate sentences may be transmitted to the interpretation terminal 60 to be displayed on it. Furthermore, it is possible to display a plurality of candidate finding sentences upon arranging them in an order corresponding to the similarities (difference degrees) calculated by the image feature information comparing unit 102.

In general, the interpretation doctor makes an image viewer and interpretation report creation software operate on the interpretation terminal 60 during interpretation. When the interpretation doctor designates a target area of a medical image displayed on the image viewer with the mouse or the like, the image data I0 of the target area is transmitted to the diagnosis support apparatus 10 together with, for example, a diagnosis support request. The diagnosis support apparatus 10 executes the above diagnosis support processing in accordance with the reception of the image data I0 and the diagnosis support request. This makes it possible to automatically display the finding candidate sentences B1 to Bm on the interpretation report creation software in the interpretation terminal 60. This can greatly improve the efficiency of the entry of findings by the interpretation doctor.

A method of accumulating case data in the case database 5 will be described next.

Referring to FIG. 3, when the interpretation doctor designates a target area of a medical image on the interpretation terminal 60, enters a finding sentence corresponding to the target area, and issues an instruction to register the data in the case database 5, the interpretation terminal 60 transmits a registration request to the diagnosis support apparatus 10. That is, the interpretation terminal 60 copies the image data I0 of the target area and a finding sentence A0 corresponding to the image data I0 and transmits them to the diagnosis support apparatus 10 together with the registration request. Upon receiving these data, the diagnosis support apparatus 10 starts the case data registration processing shown in FIG. 5.

First of all, the image feature information extraction unit 101 in FIG. 3 acquires (receives) the image data I0 of the target area and the corresponding finding sentence A0 (step S21 in FIG. 5), and then extracts the image feature information $F0_{1-x}$ from the image data I0 (step S22 in FIG. 5). A method of extracting the image feature information $F0_{1-x}$ is the same as that described in the diagnosis support processing. The image feature information extraction unit 101 then creates the data set FA constituted by the image feature information $F0_{1-x}$ and the finding sentence A0, and registers the data set FA as new case data in the case database 5 (step S23 in FIG. 5). With the above operation, the case data registration processing is terminated.

As described above, the diagnosis support apparatus according to the first embodiment can directly search for finding sentences (A1 to Am) in past interpretation reports written concerning medical images having feature information similar to the feature information ($F0_{1-x}$) of a medical image to be interpreted by using the feature information ($F0_{1-x}$). This makes it possible to overcome the drawbacks of keyword search described in the column of "BACKGROUND ART" and quote finding sentences from past interpretation reports efficiently and properly. It is therefore possible to provide a diagnosis support apparatus which automatically creates finding sentences in accordance with the contents of an image to be interpreted.

Second Embodiment

The function of a diagnosis support apparatus 10 according to the second embodiment and a processing procedure in the apparatus will be described below with reference to FIGS. 10 to 13.

Figure 10:
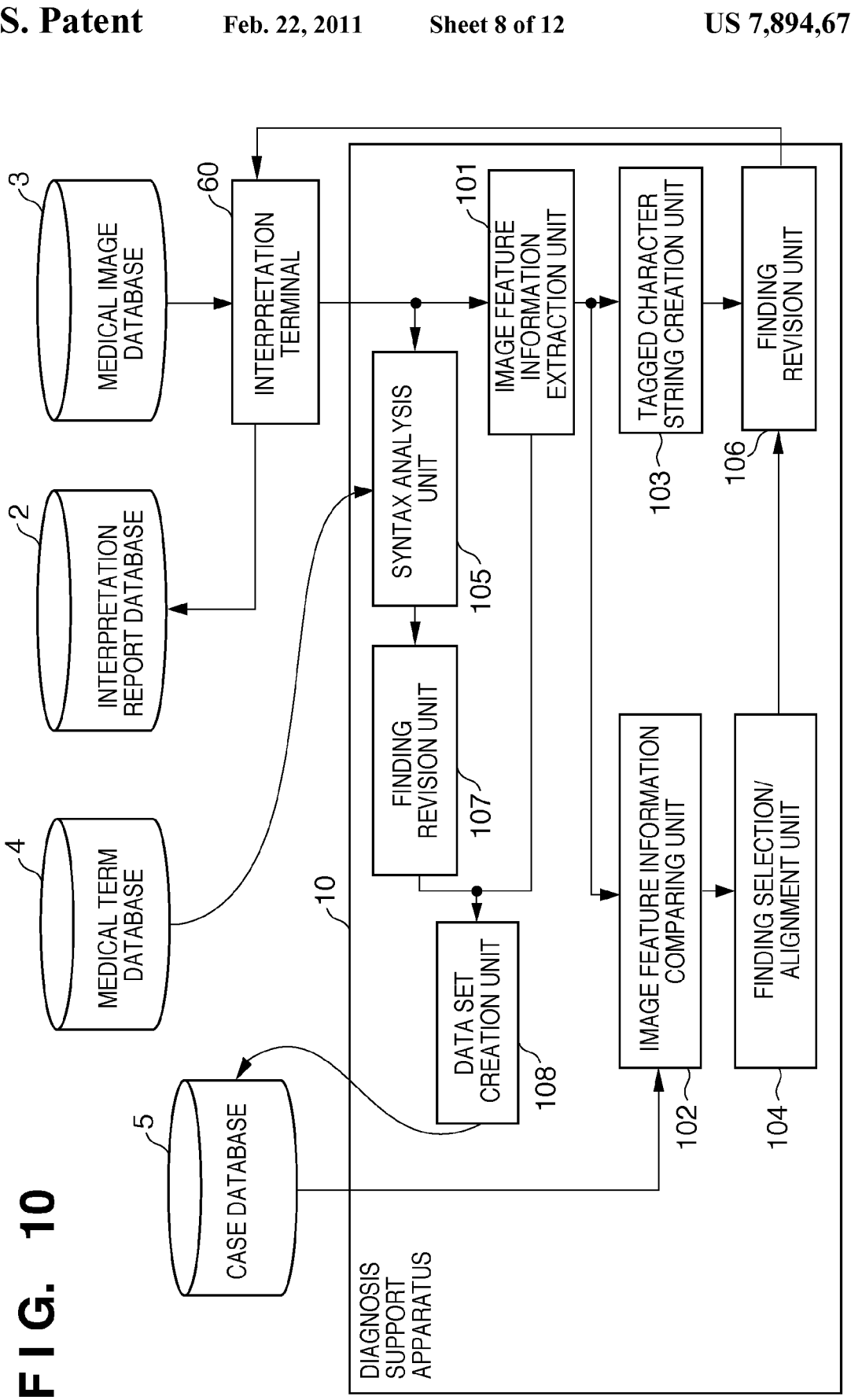
FIG. 10 is a functional block diagram for explaining the main functions of a diagnosis support apparatus 10 according to the second embodiment of the present invention.

FIG. 10 is a functional block diagram for explaining the main functions of the diagnosis support apparatus 10 according to the second embodiment. For the sake of descriptive convenience, the upper half of FIG. 10 shows the medical information system 210 shown in FIG. 2 with some of the constituent elements being omitted.

Figure 11:
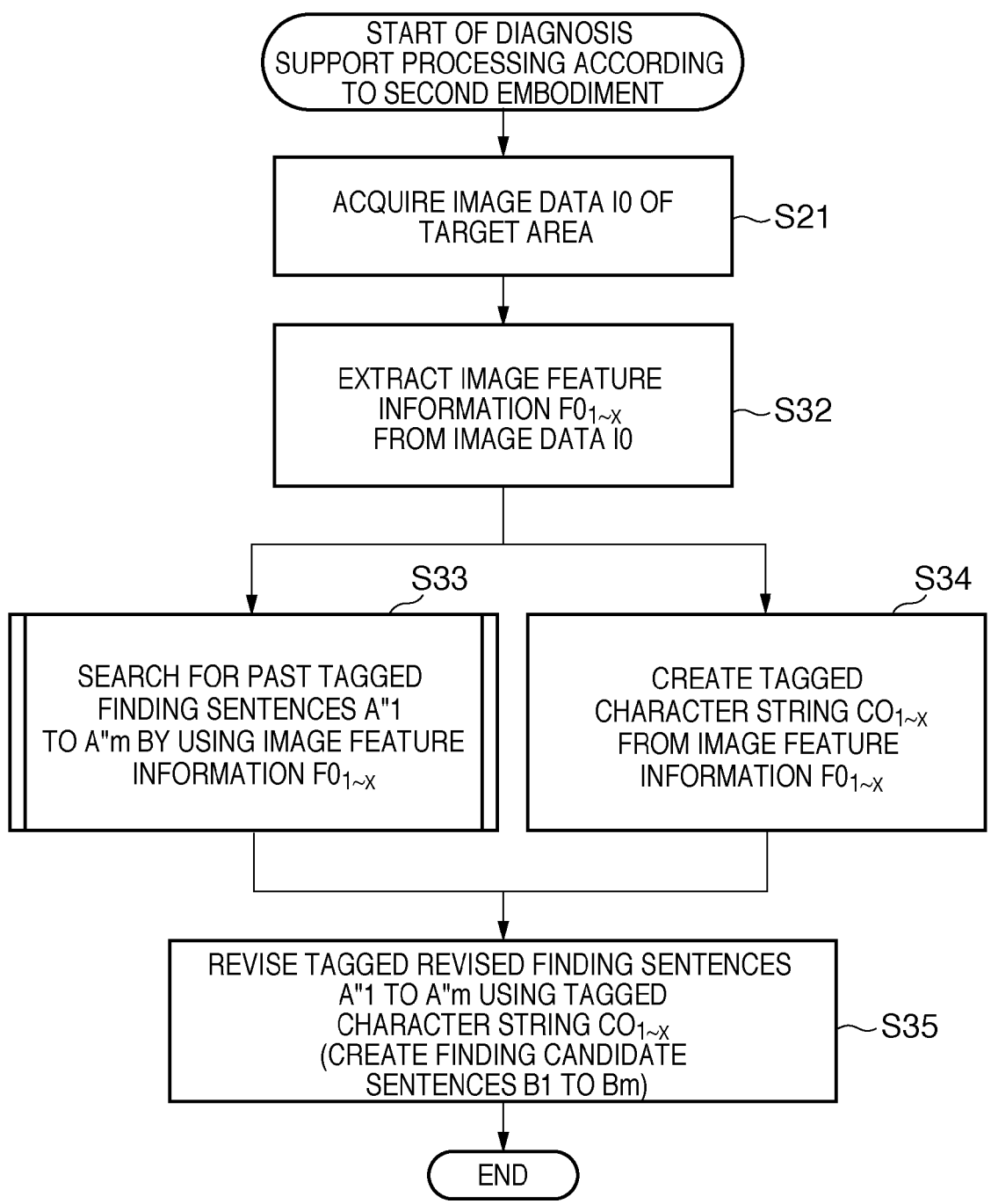
FIG. 11 is a flowchart showing a diagnosis support processing procedure in the diagnosis support apparatus 10 shown in FIG. 10.
Figure 12:
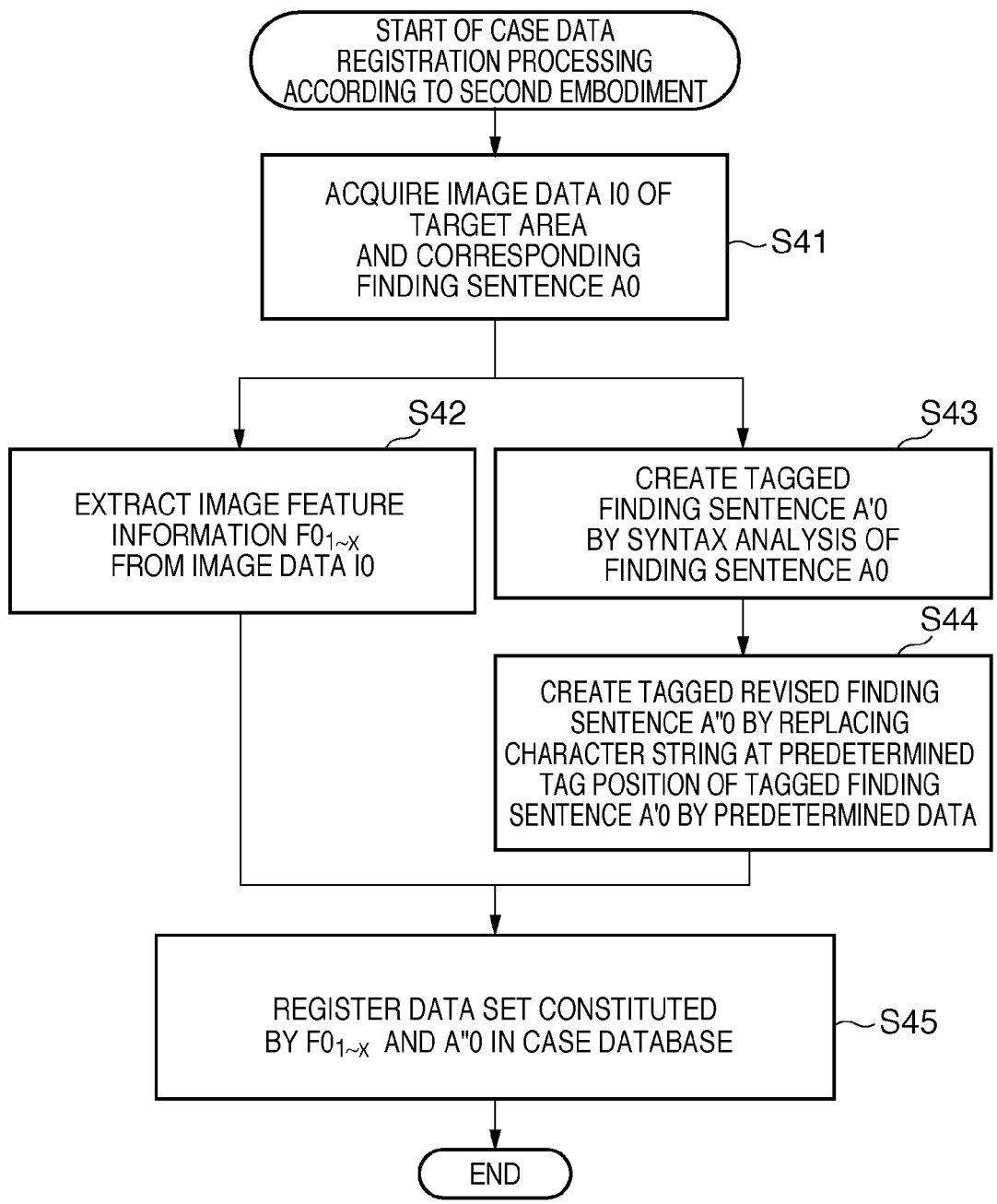
FIG. 12 is a flowchart showing a detail procedure in step S33 in diagnosis support processing in the diagnosis support apparatus 10 shown in FIG. 10.
Figure 13:
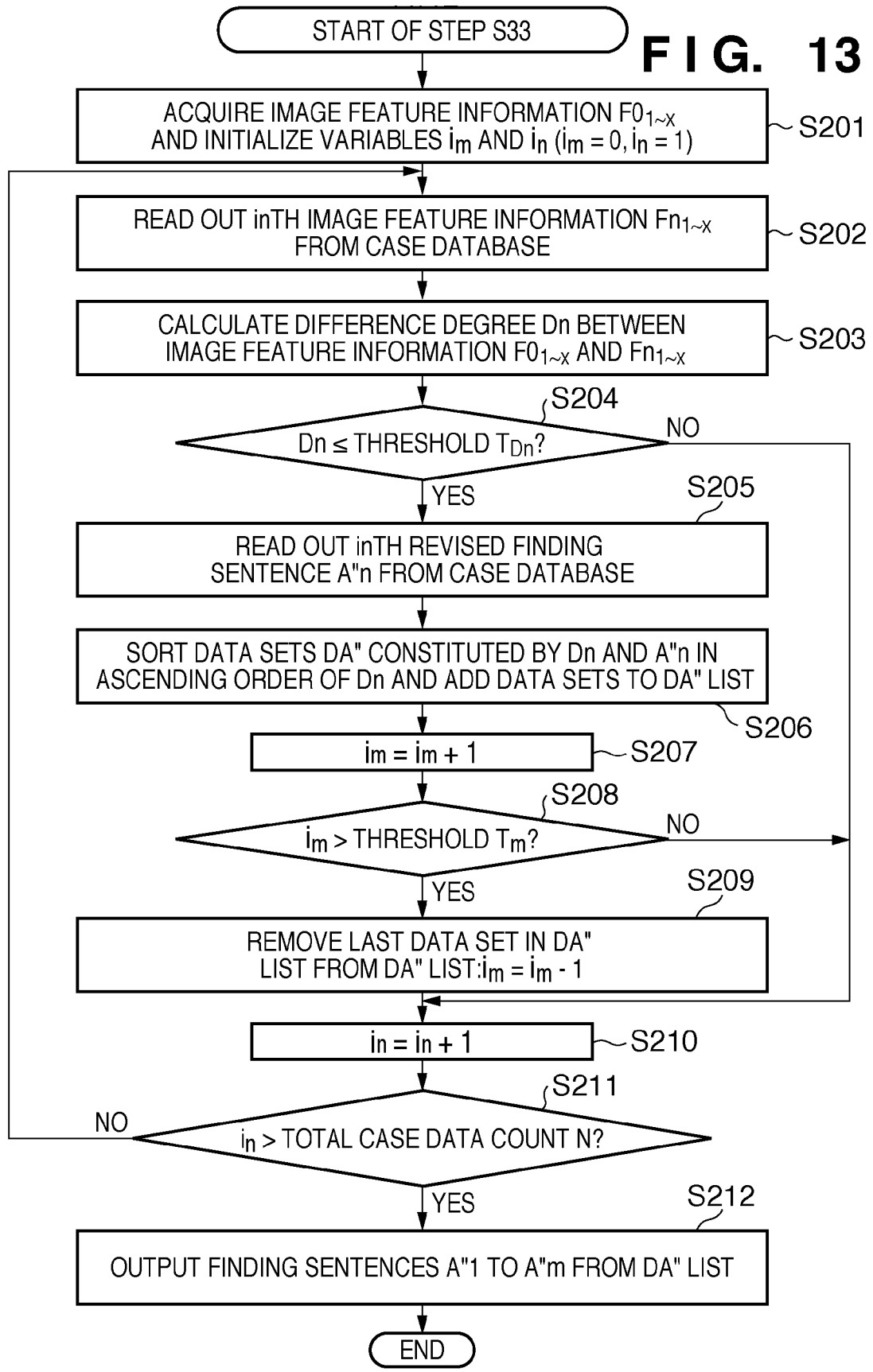
FIG. 13 is a flowchart showing a case data registration processing procedure in the diagnosis support apparatus 10 shown in FIG. 10.

FIGS. 11 to 13 are flowcharts showing processing procedures in the diagnosis support apparatus 10 shown in FIG. 10. FIG. 11 shows a procedure for diagnosis support processing. FIG. 12 shows a detailed procedure in step S33 in the diagnosis support processing. FIG. 13 shows a procedure for case data registration processing.

Since the functional blocks and processing procedures are mostly the same as those in the first embodiment, differences from the first embodiment will be mainly described below.

A great difference from the first embodiment resides in the timing at which a tagged finding sentence is created by performing syntax analysis of a finding sentence. The first embodiment creates the tagged finding sentences A'1 to A'm in the diagnosis support processing (step S14 in FIG. 4). In contrast, the second embodiment creates a tagged finding sentence A'0 of a finding sentence A0 in case data registration processing (step S43 in FIG. 12). A procedure for case data registration processing in the second embodiment will be described below.

In the case data registration processing in the second embodiment, first of all, a syntax analysis unit 105 performs syntax analysis of a finding sentence as an interpretation result to be registered, and extracts a description corresponding to each feature item of image feature information. A finding revision unit 107 then assigns a tag indicating a feature item to the extracted description, and replaces the tagged description with a predetermined description, thereby creating a revised finding sentence. A data set creation unit 108 associates the created revised finding sentence with the image feature information extracted by an image feature information extraction unit 101 and registers them as one data set in the case database 5.

Referring to FIG. 10, when an interpretation terminal 60 transmits image data I0 of the target area and a corresponding finding sentence A0 to a diagnosis support apparatus 10, the diagnosis support apparatus 10 acquires (receives) these data (step S41 in FIG. 12). Note however that in the second embodiment, both the image feature information extraction unit 101 and the syntax analysis unit 105 of the diagnosis support apparatus 10 receive the image data I0 and the finding sentence A0.

The image feature information extraction unit 101 extracts image feature information $F0_{1-x}$ from the received image data I0 of the target area, and transfers the information to the data set creation unit 108 (step S42 in FIG. 12). On the other hand, the syntax analysis unit 105 performs syntax analysis of the received finding sentence A0. Upon finding a term corresponding to the image feature information $F0_{1-x}$, the syntax analysis unit 105 assigns a dedicated tag determined in advance for each image feature information to the term to create the tagged finding sentence A'0 (step S43 in FIG. 12).

The finding revision unit 107 checks the tagged finding sentence A'0 received from the syntax analysis unit 105. When finding predetermined tags, the finding revision unit 107 replaces the character strings assigned with the tags by predetermined special data (character strings, symbols, numerical values, and the like). In this manner, the finding revision unit 107 creates a tagged revised finding sentence A"0 (step S44 in FIG. 12).

The data set creation unit 108 creates a data set FA" constituted by the image feature information $F0_{1-x}$ received from the image feature information extraction unit 101 and the tagged revised finding sentence A"0 received from the finding revision unit 107. The data set creation unit 108 then registers the data set FA" as new case data in a case database 5 (step S45 in FIG. 12). In this case, the case database 5 compares the case data which have already been registered with the case data to be newly registered to determine whether case data which is completely identical or almost identical (a different portion falls within a predetermined range) has existed. Upon determining that such data has existed, the case database 5 performs control not to register the new case data. With the above operation, the case data registration processing is terminated.

Performing the above case data registration processing in the second embodiment can have the merit of avoiding the repetitive registration of the almost identical data set FA" when the similar data set FA" has already been registered in the case database 5. That is, if only a character string, in the finding sentence A0, which corresponds to image feature information (e.g., a body region name or an abnormal area size) determined in advance to be replaced differs from a registered finding sentence, an identical finding sentence is obtained by converting the finding sentence A0 into the tagged revised finding sentence A"0. If, therefore, finding sentences whose image feature information $F0_{1-x}$ is also almost identical to that of a registered finding sentence (different portions fall within a predetermined range), the registration of redundant case data can be avoided by removing them.

In the procedure for the diagnosis support processing (FIGS. 11 and 13) in the second embodiment, "the past finding sentences A1 to Am" and "the tagged finding sentences A'1 to A'm" in the first embodiment may be replaced by "tagged revised finding sentences A"1 to A"m. That is, an image feature information comparing unit 102 acquires a revised finding sentence corresponding to image feature information similar to the image feature information of the target area from the case database 5. A finding selection/alignment unit 104, tagged character string creation unit 103, and finding revision unit 106 create a finding sentence concerning the target area by changing a predetermined description (a portion replaced by special data) included in the acquired revised finding sentence based on the image feature information of the target area. In this case, the predetermined description is detected based on the tag. Step S14 in FIG. 4 is processing to be executed by the syntax analysis unit 105 in FIG. 3. In the second embodiment, however, since the past finding sentence acquired from the case database 5 has already been a tagged finding sentence, this processing need not be executed. For this reason, the processing in FIG. 11 includes no step corresponding to step S14 in FIG. 4.

Note that the finding revision unit 107 may create a tagged finding sentence by assigning a tag indicating a feature item to an extracted description, and the data set creation unit 108 may register the created tagged finding sentence in the case database 5 in association with the corresponding image feature information. In this case, the image feature information comparing unit 102 acquires a tagged finding sentence corresponding to image feature information similar to the image feature information of the target region from the case database 5. The finding selection/alignment unit 104, the tagged character string creation unit 103, and the finding revision unit 106 then create a finding sentence by changing the tagged description included in the acquired tagged finding sentence based on the contents of the corresponding feature item of the image feature information of the target area. Note however that it is not possible to avoid the redundancy of a description in the case database 5, unlike in the case in which a revised finding sentence is registered.

Third Embodiment

The first and second embodiments register the data set FA (or FA") constituted by the image feature information $F0_{1-x}$ and the finding sentence A0 (or the tagged revised finding sentence A"0) in the case database 5. The third embodiment stores reliability information indicating the reliability of each finding sentence stored in a case database 5. An image feature information comparing unit 102 acquires a finding sentence whose reliability represented by reliability information exceeds a predetermined value among the finding sentences stored in the case database 5 in correspondence with pieces of image feature information whose similarities with the image feature information of the target area exceed a threshold. In particular, the third embodiment uses, as reliability information, information concerning the evaluation of the interpretation doctor who has created a finding sentence. More specifically, this embodiment registers a data set FA upon adding an identifier for identifying the doctor who has performed interpretation (to be simply referred to as a doctor ID hereinafter) to the data set. That is, case data accumulated in the case database 5 each are constituted by three types of data, namely a doctor ID, image feature information $F_{1-x}$, and a finding sentence A (or a tagged revised finding sentence A"0).

In addition, the case database 5 or a diagnosis support apparatus 10 may store a doctor information table in which information concerning doctor IDs is written. In this doctor information table, information concerning the ability of interpretation or the reliability of an interpretation result, e.g., the number of years of experience in interpretation of the doctor or the evaluation of the doctor within the hospital, is registered in advance. This makes it possible to meet the requirement made by the interpretation doctor using an interpretation terminal 60 when he/she wants to obtain finding candidate sentences B1 to Bm by selectively using only data, of the past case data, which exhibit high reliability. The following is a processing procedure for such a case.

Figure 14:
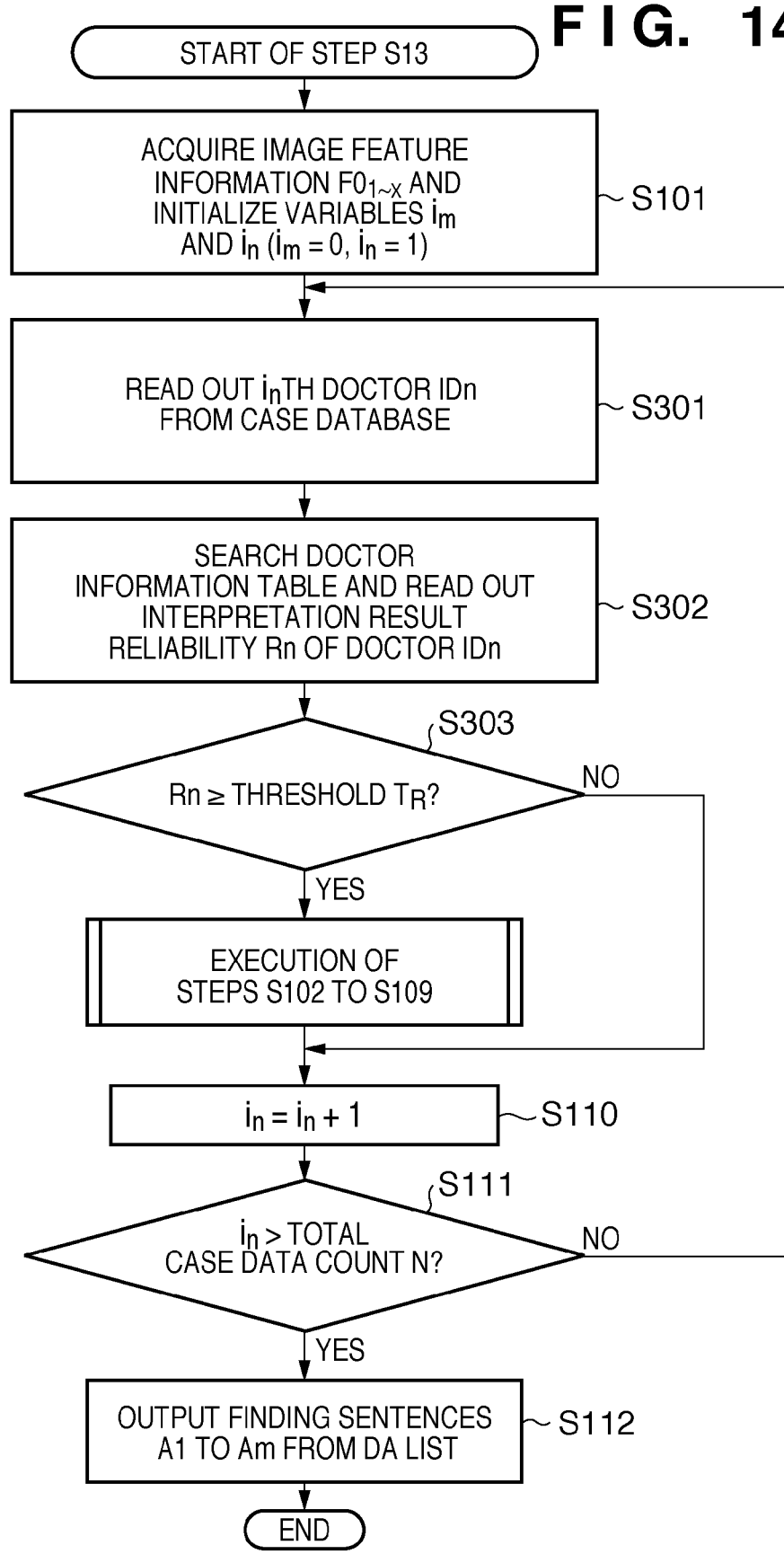
FIG. 14 is a flowchart having additional processing inserted between steps S101 and S102 in FIG. 6 in the detailed procedure in step S13 in diagnosis support processing in a diagnosis support apparatus 10 according to the third embodiment of the present invention.

The basic processing procedure is the same as that in the first embodiment. A main difference from the first embodiment is that an interpretation doctor needs to input (or designate or select) a threshold $T_R$ for required interpretation result reliability to the interpretation terminal 60. The interpretation terminal 60 also needs to transmit the threshold $T_R$ for interpretation result reliability to the diagnosis support apparatus 10 to allow it to use the threshold in step S303 in FIG. 14. In addition, some additional processing is inserted between step S101 and step S102 in FIG. 6. FIG. 14 is a flowchart in which the additional processing is inserted.

Referring to FIG. 14, the processing from step S301 to step S303 is the additional processing. First of all, in step S101, as in the first embodiment, the image feature information comparing unit 102 acquires the image feature information $F0_{1-x}$ of the target area selected from the image to be interpreted, and initializes variables $i_m$ and $i_n$ to the values 0 and 1, respectively. In step S301, the image feature information comparing unit 102 reads out an $i_n$th doctor IDn from the case database 5. In step S302, the image feature information comparing unit 102 searches the above doctor information table and reads out an interpretation result reliability Rn corresponding to the doctor IDn. In step S303, the image feature information comparing unit 102 compares the interpretation result reliability Rn with the designated threshold $T_R$ for interpretation result reliability. If the comparison result shows that Rn is equal to or more than $T_R$, the image feature information comparing unit 102 determines that the interpretation result satisfies the required reliability, and executes the processing in steps S102 to S109 described in the first embodiment. In contrast, if Rn is less than $T_R$, the image feature information comparing unit 102 determines that the interpretation result does not satisfy the required reliability, and the process advances to step S110. As described above, the first to third embodiments overcome the drawbacks of keyword search in search for past finding sentences and can quote past finding sentences more efficiently and properly. This makes it possible to provide a diagnosis support apparatus which automatically creates finding sentences in accordance with the contents of an image to be interpreted.

Although each of the above embodiments has described one type of similarity calculation method (difference degree calculation method), the similarity calculation method to be used is not limited to that in each embodiment described above. For example, in the above embodiments, the similarity (difference degree) between the pieces of image feature information $F0_{1-x}$ and $Fn_{1-x}$ is defined as the linear sum of the differences between the respective pieces of image feature information. More generally, if $F0_{1-x}$ and $Fn_{1-x}$ are described as x-dimensional vectors VF0 and VFn, the similarity (difference degree) can be reworded as the distance between the two vectors (VF0 and VFn). For example, obtaining the square linear sum (its square root) of the differences between the respective pieces of image feature information is equivalent to obtain the Euclidean distance between the two vectors. In addition, in the mathematical field, various inter-vector distances are defined. All these definitions can be used as the definitions of similarity (difference degree) in the above embodiments. It is also possible to prepare a plurality of types of similar calculation methods and allow a doctor as a user to designate his/her desired calculation method.

The embodiments have been explained in detail. The present invention can adopt embodiments in the form of, for example, a system, apparatus, method, program, or storage medium. More specifically, the present invention may be applied to either a system configured by a plurality of devices or an apparatus consisting of a single device.

Note that the present invention includes a case in which the functions of the embodiments are achieved when a software program is directly or remotely supplied to a system or apparatus, and a computer of that system or apparatus reads out and executes the supplied program code. The program to be supplied in this case is a computer program corresponding to each illustrated flowchart in the embodiments.

Therefore, the program code itself installed in a computer to implement the functional processing of the present invention using the computer implements the present invention. Put differently, the present invention includes the computer program itself for implementing the functional processing of the present invention.

In this case, the form of program is not particularly limited, and an object code, a program to be executed by an interpreter, and script data to be supplied to an OS may be used as long as they have the functions of the program.

As a computer-readable storage medium for supplying the computer program, the following media can be used. For example, a Floppy® disk, hard disk, optical disk, magneto-optical disk, MO, CD-ROM, CD-R, CD-RW, magnetic tape, nonvolatile memory card, ROM, and DVD (DVD-ROM, DVD-R) can be used.

As another program supply method, the user establishes connection to a homepage on the Internet using a browser on a client computer, and downloads the computer program of the present invention from the homepage onto a recording medium such as a hard disk. In this case, the program to be downloaded may be a compressed file including an automatic installation function. Also, program codes that form the program of the present invention may be divided into a plurality of files, which may be downloaded from different homepages. That is, the present invention includes a WWW server which makes a plurality of users download program files required to implement the functional processing of the present invention by the computer.

Also, a storage medium such as a CD-ROM, which stores the encrypted program of the present invention, may be delivered to the user. In this case, the user who has cleared a predetermined condition may be allowed to download key information used to decrypt the encrypted program from a homepage via the Internet. The user executes the encrypted program using the key information to install the program on a computer.

The functions of the aforementioned embodiments can be implemented when the computer executes the readout program. Furthermore, the functions of the aforementioned embodiments may be implemented in cooperation with an OS or the like running on the computer based on an instruction of that program. In this case, the OS or the like executes some or all of actual processes, which implement the functions of the aforementioned embodiments.

Furthermore, some or all of the functions of the aforementioned embodiments may be implemented when the program read out from the storage medium is written in a memory equipped on a function expansion board or a function expansion unit, which is inserted in or connected to the computer. In this case, after the program is written in the function expansion board or unit, a CPU equipped on the function expansion board or unit executes some or all of actual processes based on an instruction of that program.

Note that the description in each of the above embodiments is an example of a preferred diagnosis support apparatus according to the present invention. The present invention is not limited to this.

That is, the present invention is not limited to the aforementioned embodiments, and various changes and modifications can be made without departing from the spirit and scope of the present invention. Therefore, to apprise the public of the scope of the present invention, the following claims are appended.

This application claims the benefit of Japanese Patent Application No. 2007-256014, filed Sep. 28, 2007, which is hereby incorporated by reference herein in its entirety.

The invention claimed is:

1. A diagnosis support apparatus comprising:
    a storage unit configured to store image feature information and a finding sentence as an interpretation result in correspondence with each other;
    an acquisition unit configured to acquire image feature information of a target area designated on an image to be interpreted;
    a search unit configured to search said storage unit for image feature information similar to the image feature information acquired by said acquisition unit and acquire a finding sentence stored in correspondence with the retrieved image feature information from said storage unit; and a creation unit configured to created a finding sentence concerning interpretation of the designated target area by changing, based on image feature information of the target area acquired by said acquisition unit, a description of the finding sentence acquired by said search unit, wherein said creation unit comprises:

an extraction unit configured to extract a description corresponding to each feature item of image feature information by performing syntax analysis of the finding sentence acquired by said search unit; and a changing unit configured to change the description extracted by said extraction unit, based on a content of each feature item of the image feature information of the target area.

2. The diagnosis support apparatus according to claim 1, wherein said search unit calculates a similarity between the image feature information of the target area and image feature information stored in said storage unit, and acquires a finding sentence stored in correspondence with image feature information corresponding to a calculated similarity exceeding a threshold.

3. The diagnosis support apparatus according to claim 2, further comprising a designation unit configured to designate a similarity calculation method in said search unit.

4. The diagnosis support apparatus according to claim 1, further comprising a registration unit configured to receive a sentence as an interpretation result to be registered and image feature information and register the sentence and the image feature information in said storage unit in association with each other.

5. The diagnosis support apparatus according to claim 1, wherein said search unit calculates a similarity between the image feature information of the target area and image feature information stored in said storage means, and acquires a plurality of finding sentences stored in correspondence with image feature information corresponding to a calculated similarity exceeding a threshold, and said creation unit creates a plurality of candidate finding sentences of a finding sentence concerning the target area by using the plurality of finding sentences acquired by said search unit.

6. The diagnosis support apparatus according to claim 5, further comprising a removal unit configured to remove candidate finding sentences having the same content from the plurality of candidate finding sentences.

7. The diagnosis support apparatus according to claim 5, wherein said creation unit further comprises an alignment unit configured to display the plurality of candidate finding sentences on a display unit upon arranging the plurality of candidate finding sentences in an order corresponding to similarities in said search unit.

8. The diagnosis support apparatus according to claim 1, wherein said storage unit further stores reliability information indicating a reliability of each finding sentence, and said search unit acquires a finding sentence whose reliability indicated by reliability information exceeds a predetermined value among finding sentences stored in correspondence with pieces of image feature information, stored in said storage means, whose similarities with the image feature information of the target area exceed a threshold.

9. The diagnosis support apparatus according to claim 8, wherein as the reliability information of the sentence, information concerning an evaluation of an interpretation doctor who has created the finding sentence is used.

10. A diagnosis support apparatus comprising:

a storage unit configured to store image feature information and a finding sentence as an interpretation result in correspondence with each other;

an acquisition unit configured to acquire image feature information of a target area designated on an image to be interpreted;

a search unit configured to search said storage unit for image feature information similar to the image feature information acquired by said acquisition unit and acquire a finding sentence stored in correspondence with the retrieved image feature information from said storage unit;

a creation unit configured to create a finding sentence concerning interpretation of the designated target area by changing, based on image feature information of the target area acquired by said acquisition unit, a description of the finding sentence acquired by said search unit; and a registration unit configured to extract a description corresponding to each feature item of image feature information by performing syntax analysis of a finding sentence as an interpretation result to be registered, assign a tag indicating a feature item to the extracted description, create a revised finding sentence by replacing the description assigned with the tag by a predetermined description, and register the created revised finding sentence in said storage unit in association with corresponding image feature information, wherein said search unit acquires a revised finding sentence corresponding to image feature information similar to the image feature information of the target area from said storage unit, and said creation unit creates a finding sentence concerning the target area by changing the predetermined description included in the revised finding sentence acquired by said search unit based on the image feature information of the target area.

11. A diagnosis support apparatus comprising:

a storage unit configured to store image feature information and a finding sentence as an interpretation result in correspondence with each other;

an acquisition unit configured to acquire image feature information of a target area designated on an image to be interpreted;

a search unit configured to search said storage unit for image feature information similar to the image feature information acquired by said acquisition unit and acquire a finding sentence stored in correspondence with the retrieved image feature information from said storage unit;

a creation unit configured to create a finding sentence concerning interpretation of the designated target area by changing, based on image feature information of the target area acquired by said acquisition unit, a description of the finding sentence acquired by said search unit; and a registration unit configured to extract a description corresponding to each feature item of image feature information by performing syntax analysis of a finding sentence as an interpretation result to be registered, create a tagged finding sentence by assigning a tag indicating a feature item to the extracted description, and register the created tagged finding sentence in said storage unit in association with corresponding image feature information, wherein said search unit acquires a tagged finding sentence corresponding to image feature information similar to the image feature information of the target area from said storage unit, and said creation unit creates a finding sentence concerning the target area by changing, based on a content of a feature item corresponding to the image feature information of the target area, a tagged description included in the tagged finding sentence acquired by said search unit.

12. A diagnosis support apparatus comprising:
a storage unit configured to store image feature information and a finding sentence in correspondence with each other;
an acquisition unit configured to acquire image feature information of an image to be interpreted;
a search unit configured to search for a finding sentence stored in said storage unit, based on the image feature information acquired by said acquisition unit; and
a creation unit configured to create a finding sentence concerning the image to be interpreted, based on a description of a finding sentence acquired by said search unit,
wherein said creation unit comprises:
an extraction unit configured to extract a description corresponding to each feature item of image feature information by performing syntax analysis of a finding sentence acquired by said search unit; and
a changing unit configured to change the description extracted by said extraction unit, based on a content of each feature item of image feature information of a target area.

13. A control method for a diagnosis support apparatus comprising storage means for storing image feature information and a finding sentence as an interpretation result in correspondence with each other, characterized by comprising:
an acquisition step of acquiring image feature information of a target area designated on an image to be interpreted;
a search step of searching the storage means for image feature information similar to the image feature information acquired in the acquisition step and acquiring a finding sentence stored in correspondence with the retrieved image feature information from the storage means; and
a creation step of creating a finding sentence concerning interpretation of the designated target area by changing, based on image feature information of the target area acquired in the acquisition step, a description of the finding sentence acquired in the search step,
wherein said creation step comprises:
a extraction step of extracting a description corresponding to each feature item of image feature information by performing syntax analysis of the finding sentence acquired in the search step; and
a changing step of changing the description extracted in the extraction step, based on a content of each feature item of the image feature information of the target area.

14. A computer-readable storage medium storing a program for making a computer execute a control method defined in claim 13.

15. A control method for a diagnosis support apparatus comprising storage means for storing image feature information and a finding sentence in correspondence with each other, characterized by comprising:
an acquisition step of acquiring image feature information of an image to be interpreted;
a search step of searching for a finding sentence stored in the storage means, based on the image feature information acquired in the acquisition step; and
a creation step of creating a finding sentence concerning the image to be interpreted, based on a description of a finding sentence acquired in the search step,
wherein the creation step comprises:
an extraction step of extracting a description corresponding to each feature item of image feature information by performing syntax analysis of a finding sentence acquired in the search step; and
a changing step of changing the description extracted in the extraction step, based on a content of each feature item of image feature information of a target area.

16. A control method for a diagnosis support apparatus comprising storage means for storing image feature information and a finding sentence as an interpretation result in correspondence with each other, characterized by comprising:
an acquisition step of acquiring image feature information of a target area designated on an image to be interpreted;
a search step of searching said storage means for image feature information similar to the image feature information acquired in the acquisition step and acquiring a finding sentence stored in correspondence with the retrieved image feature information from said storage means;
a creation step of creating a finding sentence concerning interpretation of the designated target area by changing, based on image feature information of the target area acquired in the acquisition step, a description of the finding sentence acquired in the search step; and
a registration step of extracting a description corresponding to each feature item of image feature information by performing syntax analysis of a finding sentence as an interpretation result to be registered, assigning a tag indicating a feature item to the extracted description, creating a revised finding sentence by replacing the description assigned with the tag by a predetermined description, and registering the created revised finding sentence in said storage means in association with corresponding image feature information,
wherein the search step acquires a revised finding sentence corresponding to image feature information similar to the image feature information of the target area from said storage means, and
the creation step creates a finding sentence concerning the target area by changing the predetermined description included in the revised finding sentence acquired in the search step based on the image feature information of the target area.

17. A control method for a diagnosis support apparatus comprising storage means for storing image feature information and a finding sentence as an interpretation result in correspondence with each other, characterized by comprising:
an acquisition step of acquiring image feature information of a target area designated on an image to be interpreted;
a search step of searching said storage means for image feature information similar to the image feature information acquired in the acquisition step and acquiring a finding sentence stored in correspondence with the retrieved image feature information from said storage means;
a creation step of creating a finding sentence concerning interpretation of the designated target area by changing, based on image feature information of the target area acquired in the acquisition step, a description of the finding sentence acquired in the search step; and a registration step of extracting a description corresponding to each feature item of image feature information by performing syntax analysis of a finding sentence as an interpretation result to be registered, creating a tagged finding sentence by assigning a tag indicating a feature item to the extracted description, and registering the created tagged finding sentence in said storage means in association with corresponding image feature information, wherein the search step acquires a tagged finding sentence corresponding to image feature information similar to the image feature information of the target area from said storage means, and the creation step creates a finding sentence concerning the target area by changing, based on a content of a feature item corresponding to the image feature information of the target area, a tagged description included in the tagged finding sentence acquired in the search step.

* * * * *